(12) United States Patent
Thompson

(10) Patent No.: US 8,038,947 B2
(45) Date of Patent: Oct. 18, 2011

(54) ANALYTE SENSOR DEVICES AND HOLDERS, AND METHODS AND SYSTEMS UTILIZING THE SAME

(75) Inventor: Richard B. Thompson, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 66 days.

(21) Appl. No.: 12/099,952

(22) Filed: Apr. 9, 2008

(65) Prior Publication Data

US 2009/0042311 A1    Feb. 12, 2009

Related U.S. Application Data

(60) Provisional application No. 60/910,687, filed on Apr. 9, 2007.

(51) Int. Cl.
*G01N 21/64* (2006.01)
(52) U.S. Cl. .............. 422/82.07; 422/68.1; 422/82.05; 422/82.06; 422/82.08
(58) Field of Classification Search .................. None
See application file for complete search history.

(56) References Cited

U.S. PATENT DOCUMENTS

| | | | |
|---|---|---|---|
| 5,094,819 A | 3/1992 | Yager et al. | |
| 5,496,522 A | 3/1996 | Vo-Dinh et al. | |
| 5,545,517 A | 8/1996 | Thompson et al. | |
| 5,631,169 A | 5/1997 | Lakowicz et al. | |
| 5,747,349 A | 5/1998 | van den Engh et al. | |
| 5,952,236 A | 9/1999 | Thompson et al. | |
| 6,197,258 B1 | 3/2001 | Thompson et al. | |
| 6,225,127 B1 | 5/2001 | Thompson et al. | |
| 6,284,544 B1 | 9/2001 | Thompson et al. | |
| 6,340,598 B1 | 1/2002 | Herron et al. | |
| 7,022,515 B2 | 4/2006 | Herron et al. | |
| 7,556,934 B2 * | 7/2009 | Ragless | .................... 435/14 |

FOREIGN PATENT DOCUMENTS

| | | |
|---|---|---|
| EP | 601714 | 6/1994 |
| EP | 1683868 | 7/2006 |

OTHER PUBLICATIONS

Kiyonaka, Shigeki, et al. Semi-wet peptide/protein array using supermolecular hydrogel, 2004, Nature Materials, vol. 3, pp. 58-64.*
Boca Scientific, retrieved from internet:http://www.bocascientific.com/papain-immobilized-on-matrix-f7m-1-column-p-838.html.*

(Continued)

*Primary Examiner* — Yelena G Gakh
*Assistant Examiner* — Robert Xu
(74) *Attorney, Agent, or Firm* — Kristina Castellano; Castellano PLLC

(57) ABSTRACT

Provided are sensor devices, methods, systems, and kits for measuring the concentration of at least one target analyte. Sensor devices may be mounted into an optical system for measuring the target analyte. Example sensor devices may also be removably mounted in a holder that enables the sensor device to be inserted into a container that allows the sensor device to contact an analyte containing sample. Further provided are methods that include contacting a sensor device with an analyte-containing sample; determining analyte concentration; and optionally repeating these steps to determine if the analyte concentration spikes or exceeds a predetermined level, which may trigger an alarm response.

8 Claims, 12 Drawing Sheets

OTHER PUBLICATIONS

Thompson et al, "Determination of Picomolar Concentrations of Metal Ions Using Fluorescence Anisotropy: Biosensing with a 'Reagentless' Enzyme Transducer", Anal. Chem. 1998, 70, 4717-4723.

Thompson et al., "Selectivity and Sensitivity of Fluorescence Lifetime-Based Metal Ion Biosensing Using a Carbonic Anhydrase Transducer", Analytical Biochemistry 267, 185-195 (1999).

Thompson et al., "Fluorescence Microscopy of Stimulated Zn(II) Release From Organotypic Cultures of Mammalian Hippocampus Using a Carbonic Anhydrase-Based Biosensor System", J. of Neuroscience Methods 96, (2000) 35-45.

Thompson et al., "Development of Calcium Current Subtypes in Isolated Rat Hippocampal Pyramidal Cells", J. Physiol. 1991, 439; 671-689.

Thompson, "Studying Zinc Biology with Fluorescence: ain't we got fun?", Current Opinion in Chemical Biology 2005, 9:526-532.

Bozym et al., "Measuring Picomolar Intracellular Exchangeable Zinc in PC-12 Cells Using a Ratiometric Fluorescence Biosensor", ACS Chem. Biol., Mar. 2006; 1(2) p. 103-111.

Zeng et al., "Real-Time Determination of Picomolar Free Cu(II) in Seawater Using a Fluorescence-Based Fiber Optic Biosensor", Anal. Chem 2003; 75(24) 6807-6812.

Fierke et al., "Fluorescence-based Biosensing of Zinc Using Carbonic Anhydrase", BioMetals 14: 205-222, 2001.

Abstract: Bernard et al. "Real-time Monitoring of Antigen-antibody Recognition on a Metal Oxide Surface by an Optical Grating Coupler Sensor", Eur. J. Biochem. Jun. 1, 1995; 230(2):416-23.

Abstract: Zhang et al. "An Optical Fiber Chemical Sensor for Mercury Ions Based on a Porphyrin Dimer", Anal Chem. Feb. 15, 2002; 74 (4):821-5.

Abstract: Kuswandi "Simple Optical Fibre Biosensor Based on Immobilised Enzyme for Monitoring of Trace Heavy Metal Ions.", Anal. Bioanal. Chem. Aug. 2003; 376(7):1104-10.

Abstract: Varma et al. "Amperometric Biosensor for the Detection of Hydrogen Peroxide Using Catalase Modified Electrodes in Polyacrylamide", J. Biotechnol. Sep. 23, 2005; 119(2):172-80.

Abstract: Qin et al. "A Fiber-Optic Fluorescence Sensor for Lithium Ion in Acetonitrile" Anal. Chem. Sep. 15, 2002; 74 (18):4757-62.

Abstract: Blyth et al. "Calcium Biosensing with a Sol-Gel Immobilized Photoprotein", Analyst Dec. 1996; 121 (12):1975-8.

* cited by examiner

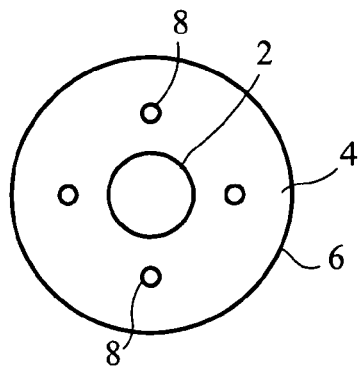
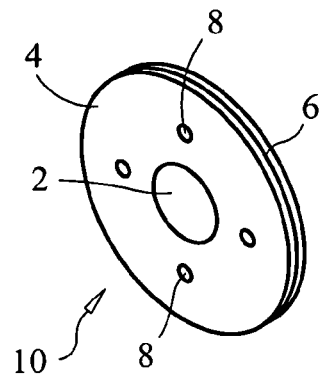
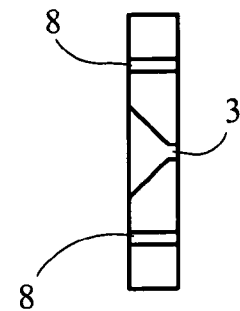
FIG. 1A  FIG. 1B  FIG. 1C
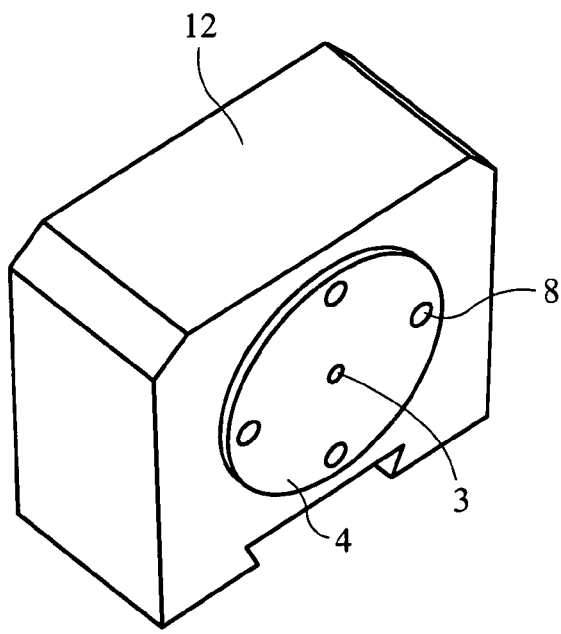
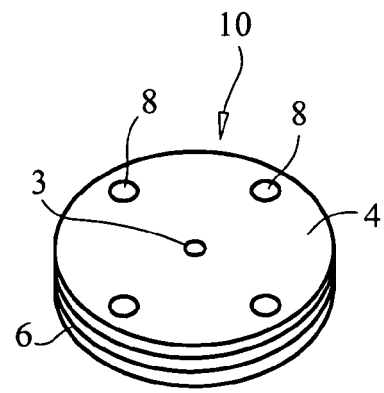
FIG. 2A  FIG. 2B

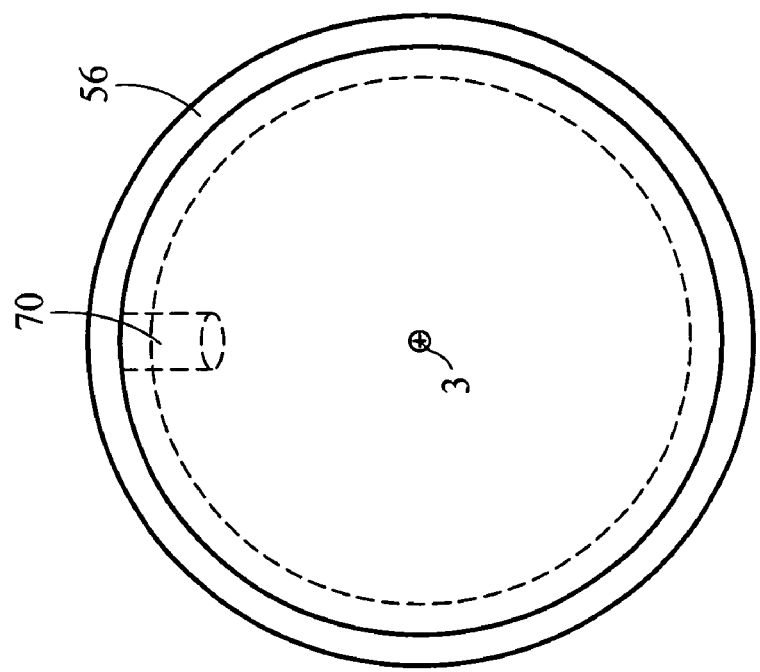
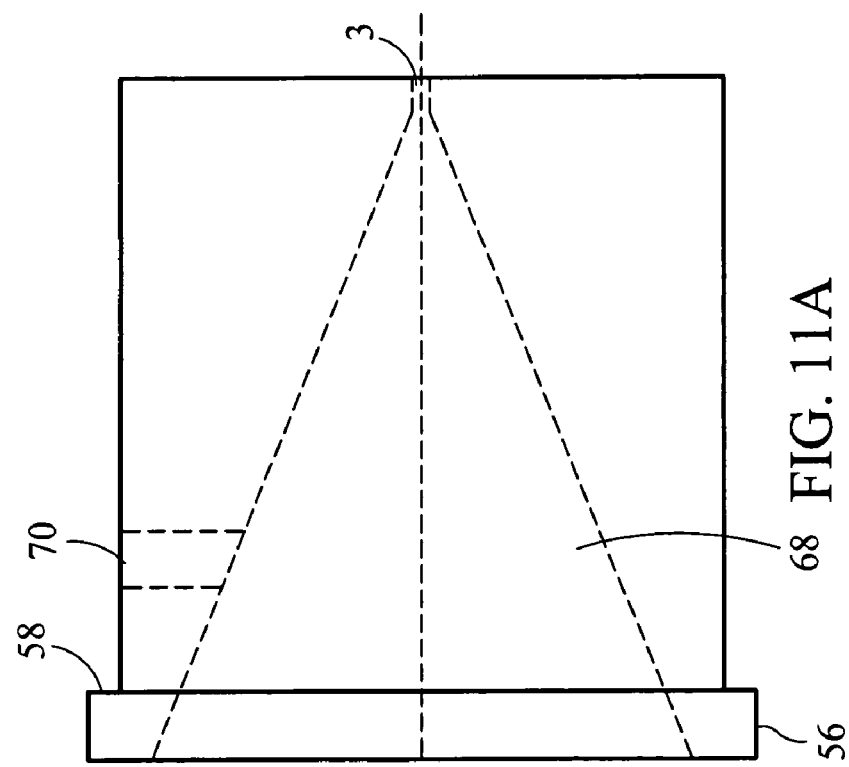
FIG. 11B
FIG. 11A

US 8,038,947 B2

ANALYTE SENSOR DEVICES AND HOLDERS, AND METHODS AND SYSTEMS UTILIZING THE SAME

RELATED APPLICATION

This application claims the benefit of U.S. Provisional Application 60/910,687 filed on Apr. 9, 2007, the contents of which are hereby incorporated by reference.

STATEMENT REGARDING FEDERALLY SPONSORED RESEARCH

Work relating to this application was performed with government support under National Science Foundation Grant No. 04 25564. The U.S. Government has certain rights in this invention.

FIELD

Example embodiments are generally directed to devices, methods, systems and kits for quantifying at least one target analyte in a sample. Example embodiments include sensor devices having at least one binding entity immobilized thereon, which binding entity is capable of binding to the at least one target analyte.

Also included are methods that include determining high or peak concentrations of a target analyte after determining the analyte concentration one or more times. Concentrations of certain absolute or relative amounts may trigger an alarm response.

BACKGROUND

Fiber optic sensors, especially fluorescence or photoluminescence-based sensors, have been used to determine analytes in solution at concentrations as low as picomolar in real time. In particular, fiber optic sensors have enabled the determination of metal ions, such as $Zn(II)$, $Cu(II)$, $Cd(II)$, $Co(II)$ and $Ni(II)$, $Fe(II)$, $Mn(II)$, $Pb(II)$, and $Hg(II)$ in aqueous solutions such as fresh water, sea water, and cerebrospinal fluid. Fiber optic sensors to determine analytes may include a binding protein or other photoluminescent or calorimetric indicator system on the fiber optic sensor, which binds with the analyte and emits a signal that can be measured. Fiber optic sensors are well suited to determining metal ions in remote (e.g., at depth in the ocean) or inaccessible (e.g., inside the living brain) circumstances. The optical design of a fiber optic probe, however, necessarily introduces background that reduces signal-to-noise ratio. Moreover, the use of fiber optic sensors is expensive and unnecessarily complex in certain circumstances, for example in the case of finite samples that have been collected and stored in bottles.

An issue with respect to binding-type assays with trace analytes in finite samples is the potential for inaccurate measurement due to the amount of binding agent. For example, if one has 20 picomolar free zinc in a liter of water and a probe is introduced (fiber optic or otherwise) that contains one nanomole of a zinc binding protein or other reversible binding zinc indicator with a zinc binding affinity (Kd) of 4 picomolar, the binding protein may bind up essentially all of the free zinc because the concentrations of both the free zinc and the binding protein are above the 4 picomolar Kd for zinc binding to the protein. The problem arises because the fractional occupancy of the binding protein may be less than 10% because all of the free zinc available in the liter of water is bound and additional binding protein remains. If instead of a liter of water, the sample were a very large, essentially infinite bath, the fractional occupancy of the binding protein would be roughly 90%, and the measurement would be more accurate. Thus, for an accurate measurement in a finite bath, a small amount of binding protein is required to obtain a higher fractional occupancy. A fiber optic may be used to introduce a small amount of binding protein on a tip of the fiber optic, but has the disadvantages mentioned above. If binding protein is dispersed throughout the water sample, the concentration of fluorophores associated with the binding protein becomes very low, and any signal is difficult to acquire.

SUMMARY

Example embodiments are generally directed to sensor devices on which at least one binding entity (such as a binding protein) is immobilized, which effectively concentrates analyte bound to the binding entity where it can be measured more easily. The binding entity is capable of generating a detectable signal upon binding of a target analyte thereto without or with the addition of a luminescent moiety such as a fluorophore. Sensor devices permit a small amount of binding entity to be immobilized thereon, to increase the fractional occupancy of the binding entity after binding to a finite amount of analyte. Sensor devices can be mounted in an optical system, such as a fluorometer, in place of a fiber optic to detect the detectable signal, but without the fiber optic.

Example embodiments are also generally directed to methods that include contacting a sensor device with a sample containing at least one target analyte; allowing the target analyte to bind with at least one binding entity immobilized on the sensor device; mounting the sensor device in an optical system; and quantifying analyte in the sample. The analyte may be quantified in the optical system by providing energy to the sensor device, where an optical mount, such as an objective holder or fiber optic connector, positions the device substantially at a focal point of energy passing through an objective lens, and measuring a detectable signal emitted by the binding entity bound to a target analyte when the sensor device receives energy.

Example embodiments are also directed to sensor device holders that include a portion capable of immobilizing a sensor device. The sensor device holder may be adapted for insertion into a container. The sensor device holder may be inserted into the container, allowing the sensor device to contact an analyte-containing sample in the container. Further example embodiments are directed to systems that include a sensor device, a sensor device holder and a container suitable for holding a sample containing at least one target analyte.

Also included are methods that include contacting a sensor device having at least one binding entity immobilized thereon, where the binding entity is capable of generating a detectable signal upon binding of a target analyte to the binding entity, with a sample containing the target analyte; determining analyte concentration from the detectable signal; and optionally repeating the contacting and determining one or more times to determine if the analyte concentration exceeds a predetermined level or has changed over a period of time, or has declined below a particular level. An alarm response may be triggered if the analyte concentration exceeds a predetermined level, has changed over time or has declined below the particular level. Example embodiments also include embodiments where a binding protein exhibits relatively slow adsorption and desorption of an analyte, such that a time-averaged signal not reflecting rapid fluctuations in the analyte concentration are obtained.

BRIEF DESCRIPTION OF THE DRAWINGS

Embodiments of the invention are herein described, by way of non-limiting example, with reference to the following accompanying drawings:

FIGS. 1A, 1B and 1C depict back, side/back and cross-sectional views, respectively, of sensor devices according to non-limiting example embodiments;

FIG. 2A depicts an objective holder having a sensor device (FIG. 2B) mounted therein, in accordance with non-limiting embodiments;

FIGS. 11A and 11B depict side and front views, respectively, of the sensor device depicted in FIGS. 9A-9C and 10A-10C;

DETAILED DESCRIPTION

Figure 3:
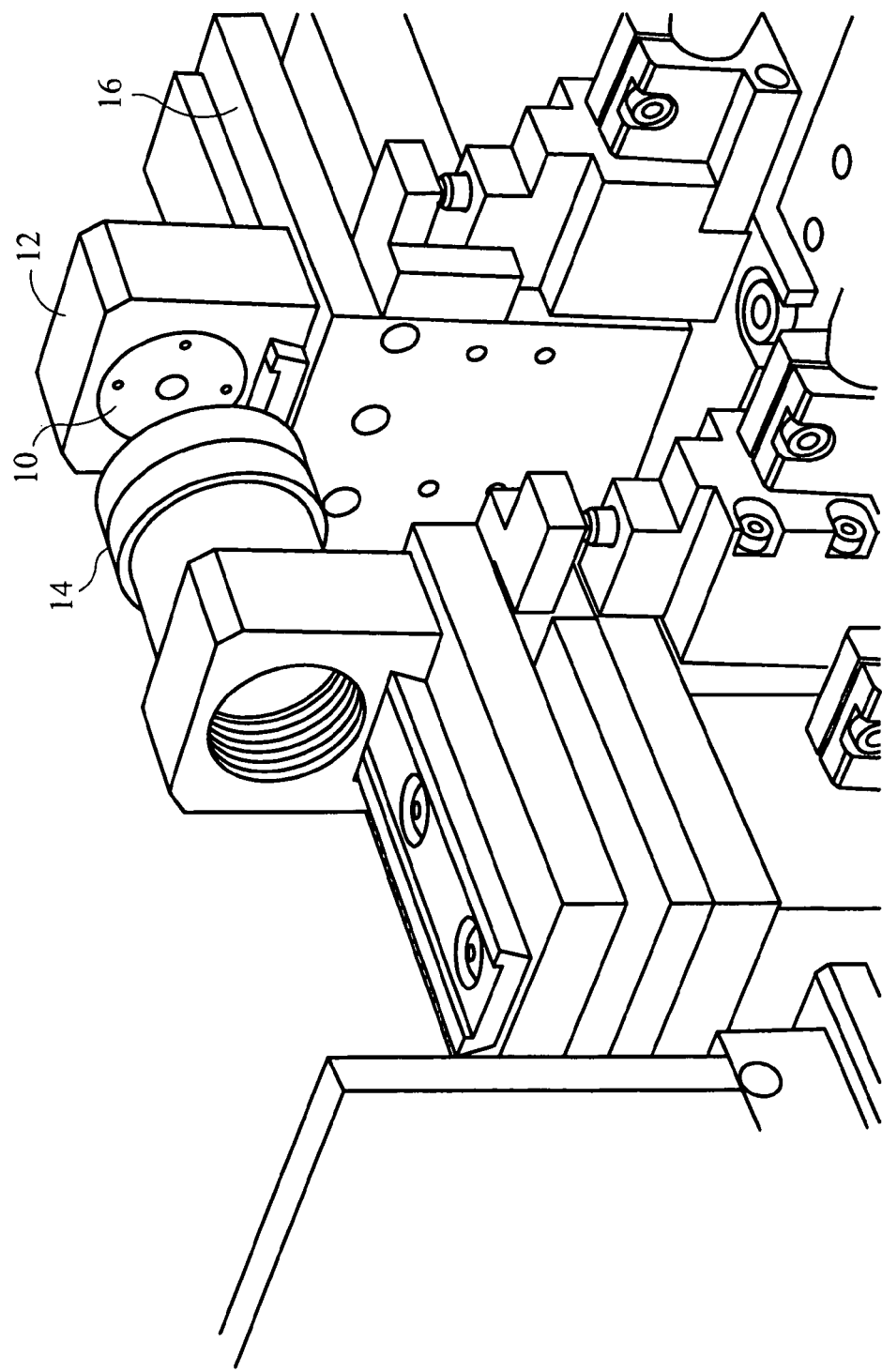
FIG. 3 depicts an objective holder having a sensor device mounted therein, where the objective holder is mounted in an optical chassis of an optical system in accordance with non-limiting embodiments.

The aspects, advantages and/or other features of example embodiments of the invention will become apparent in view of the following detailed description, which discloses various non-limiting embodiments of the invention. In describing example embodiments, specific terminology is employed for the sake of clarity. However, the embodiments are not intended to be limited to this specific terminology. It is to be understood that each specific element includes all technical equivalents that operate in a similar manner to accomplish a similar purpose. Additionally, all of the citations herein are incorporated by reference in their entirety.

Example embodiments include sensor devices, methods, systems, and kits for quantifying at least one target analyte. Example sensor devices may be mounted in a holder that enables the sensor device to be inserted into a container that allows the sensor device to contact an analyte-containing sample. Example sensor devices may also be mounted into an optical system for measuring the target analyte.

Example embodiments also include methods for determining a maximum analyte level over time or for determining if an analyte concentration spikes or exceeds a predetermined level, changes over a period of time, or has declined below a particular level, which may trigger an alarm response.

DEFINITIONS

As used herein, "a" or "an" may mean one or more. As used herein, "another" may mean at least a second or more.

The terms "analyte" and "target analyte" are used interchangeably herein and can be any molecule or compound where a concentration or quantity is desired to be measured. Examples of classes of analytes that can be measured include, but are not limited to the following: inorganic molecules such as metal ions; organic molecules including, but not limited to amino acids, peptides, polypeptides, proteins, carbohydrates, lipids, nucleotides, oligonucleotides, polynucleotides, glycoproteins or proteoglycans, lipoproteins, lipopolysaccharides, drugs, drug metabolites, small organic molecules; and natural or synthetic polymers. As used herein, a "drug" can be a known drug or a drug candidate, whose activity or effects on a particular cell type are not yet known. A "drug metabolite" is any of the by-products or the breakdown products of a drug that is changed chemically into another compound or compounds. As used herein, "small organic molecule" includes, but is not limited to, an organic molecule or compound that does not fit precisely into other classifications highlighted herein.

According to example embodiments, the target analyte may include at least one free metal ion. Non-limiting examples of free metal ions may include $Zn(II)$, $Cu(II)$, $Co(II)$, $Cd(II)$, $Ni(II)$, $Hg(II)$, $Fe(II)$, $Mn(II)$, $Pb(II)$ and other metal ions. As used herein the term "free" ion refers to a chemically active or bioavailable molecules as can be determined by those skilled in the art. The term "free" ions should be interpreted broadly to not only include molecules that are not bound, but to also include for example, molecules that may be loosely bound in solution. According to example embodiments the metal ions may bind to a binding entity such as carbonic anhydrases, proteins and/or macromolecules with greater or lesser affinity and which may measurably change the absorbance or fluorescence, as for example intensity, color, spectrum, lifetime, or fluorescence polarization (anisotropy) fluorescence themselves or promote the binding of inhibitors which quench the fluorescence.

The target analyte may be in an aqueous "sample" which is intended to include any liquid or semi-liquid composition that allows flow of the analyte (which flow may be aided by stirring, shaking or mixing) such that analyte in the sample may reach and bind to a binding entity of a device contacting the sample. By way of example a sample may be an aqueous solution such as fresh water, sea water, environmental samples, or wastewater, or it may be a biological sample such as blood, plasma, urine, or cerebrospinal fluid.

According to example embodiments an analyte and a binding entity, such as a binding protein, are binding partners. The term "associates" or "binds" as used herein refers to binding partners having a relative binding constant (Kd) sufficiently strong to allow detection of binding to the protein by a detection means. Kd may be calculated as the concentration of free analyte at which half the protein is bound, or vice versa.

Devices herein may include a one or more "binding entity." A "binding entity" is a molecule or portion thereof that binds an analyte in a specific manner. The "binding entity" may include for example a macromolecule or other binding protein. The term "macromolecule" as used herein, is meant to refer to a composition that has a molecular weight of more than 5 kD. Macromolecules can be polypeptides, proteins, nucleic acids, aptamers, polysaccharides, carbohydrates, lipids or other organic (carbon containing) or inorganic molecules. According to example embodiments, the binding entity may be any protein that is specific for an analyte of interest to which the analyte becomes reversibly bound or associated, and that can be induced to provide a signal, either directly or through a label, when such binding occurs.

As used herein, the terms "protein" and "polypeptide" are used interchangeably and are used to refer to any peptide or protein comprising two or more amino acids joined to each other by peptide bonds or modified peptide bonds. "Polypeptide" is also used to mean shorter chains, commonly referred to as peptides, oligopeptides or oligomers. According to example embodiments, a binding entity may include a single polypeptide or protein. In other embodiments, more than one binding entity may include a plurality of proteins or polypeptides. This plurality of proteins or polypeptides may make up a plurality of binding domains. In particular, according to this embodiment, one binding domain may be present for example, on each protein or polypeptide.

According to example embodiments, the binding entity may be a wild-type (native), protein or they may be a non-wild-type protein, provided that the proteins still bind to a target analyte in a specific manner. As used herein, a "non-wild-type protein" is a protein that shares substantial sequence identity with the wild-type protein. Examples of non-wild-type proteins include, but are not limited to, mutant and fusion proteins.

By way of non-limiting example, a binding entity may include wild type or variants of human carbonic anhydrase II. In particular, apocarbonic anhydrase II (CA) has a high affinity (1 pM) and outstanding selectivity for Zn(II). Alternative embodiments include, but are not limited to other human carbonic anhydrase isozymes; carbonic anhydrases from other species such as cow and spinach; other metalloenzymes including alkaline phosphatases, leucine aminopeptidases, carboxypeptidases, laccases, azurins, and ureases from diverse species; other metallo-enzymes for which inhibitor binding is metal-dependent or which bind metals exhibiting charge transfer d-d absorption bands, mutants and other variants of the above enzymes; biological, biomimetic, organic and inorganic polymers; metal-binding reagents, nucleic acids, polysaccharides, carbohydrates and nonbiological polymers may be potentially useful. Non-limiting example embodiments of carbonic anhydrase binding entities may include wild type carbonic anhydrase, L198C and H94N carbonic anhydrase or other variants or derivatives of carbonic anhydrase.

The terms "variants" and "derivatives" are used somewhat interchangeably herein. As used herein, a "derivative" of a protein or polypeptide is a protein or polypeptide that shares substantial sequence identity with the wild-type protein. Examples of derivative proteins include, but are not limited to, mutant and fusion proteins, as well as domains of a protein. Derivative proteins or polypeptides may be made or prepared by techniques known to those of skill in the art. Examples of such techniques include, but are not limited to, mutagenesis and direct synthesis.

A "mutant protein" is used herein as it is in the art. In general, a mutant protein can be created by addition, deletion or substitution of the wild-type primary structure of the protein or polypeptide. Mutations include for example, the addition or substitution of amino acid groups, non-naturally occurring amino acids, and replacement of substantially non-reactive amino acids with reactive amino acids. A mutation may serve one or more purposes. For example, a naturally occurring protein may be mutated to alter the stability of the protein, to conjugate the protein to a particular encapsulation matrix or polymer, to provide binding sites for detectable labels, to adjust its binding constant with respect to a particular analyte, or combinations of any of these purposes. Mutant proteins may be mutated to bind more than one analyte in a specific manner. Indeed, mutant proteins may possess specificity towards its wild-type analyte and another target ligand. Mutant proteins may be able to only bind an analyte or analytes that the wild-type binding protein does not bind.

Derivative proteins may also be modified, either by natural processes, such as post-translational processing, or by chemical modification techniques known in the art. Modifications can occur anywhere in the polypeptide chain, including the peptide backbone, the amino acid side-chains and the amino or carboxyl termini. It will be appreciated that the same type of modification may be present in the same or varying degrees at more than one site in a given polypeptide or protein. Also, a given polypeptide or protein may contain more than one modification. Non-limiting examples of types of modifications include: glycosylation, oxidation, iodination, glycosylation, acetylation, acylation, ADP-ribosylation, amidation, cross-linking, cyclization, disulfide bond formation, demethylation, formation of covalent cross-links, formation of cystine, formation of pyroglutamate, formylation, gamma-carboxylation, GPI anchor formation, hydroxylation, methylation, myristoylation, proteolytic processing, phosphorylation, prenylation, racemization, selenoylation, sulfation, transfer-RNA mediated addition of amino acids to proteins such as arginylation, ubiquitination, or covalent attachments of flavin, a heme moiety, a nucleotide or nucleotide derivative, or a lipid or lipid derivative.

According to example embodiments, binding entities may be selected and/or modified to alter the affinity of the binding entities towards their target analyte. In example embodiments the affinity of a binding entity may be decreased or increased depending for example on the desired use of the device or method employed.

Besides changing binding characteristics, derivative polypeptides or proteins may also used be to incorporate a labeling moiety onto or within the binding entity, such that the binding entities, e.g., polypeptides or proteins may be labeled with a labeling moiety. In example embodiments, all of the binding entities may be labeled. In other embodiments, fewer than all, but at least one of the binding entities is labeled. In other embodiments, none of the binding entities is labeled. When some or all of the binding entities are labeled, there can be one or more labeling moieties per binding entity.

Thus, according to example embodiments, binding entities may include at least one label. Labels may be used to indicate a change in the binding domains. Examples of changes in binding domains may include, but are not limited to, three-dimensional conformational changes, changes in orientation of the amino acid side chains of proteinaceous binding domains, and redox states of the binding domains.

A label can be attached to a binding entity (such as a protein) by any means known in the art. With the addition/substitution of one or more residues into a primary structure of a protein, some of the labeling moieties used in the current methods and compositions can be attached through chemical means, such as reduction, oxidation, conjugation, and condensation reactions. For example, the label may be attached via amines or carboxyl residues on a protein. Examples of residues commonly used as sites to attach labels or labeling moieties may include, but are not limited to, lysine and cysteine. For example, any thiol-reactive group may be used to attach a labeling moiety, e.g., a fluorescent label ("fluorophore"), to a naturally occurring or engineered cysteine in the primary structure of a protein. For example, iodoacetamide, bromoacetamide, or maleimide are well known thiol-reactive moieties that may be used for this purpose. Also, for example, lysine residues can be labeled using esters of N-hydroxysuccinimide or N-hydroxysulfosuccinimide.

A "labeling moiety," as used herein, is intended to mean a chemical compound or ion that possesses or comes to possess a detectable non-radioactive signal. Examples of labeling moieties include, but are not limited to, transition metals, lanthanide ions and other chemical compounds. The non-radioactive signals include, but are not limited to, fluorescence, phosphorescence, bioluminescence, electrogenerated chemiluminescence and chemiluminescence.

According to example embodiments the binding entity may be labeled with at least one photoluminescent label available to those skilled in the art. Non-limiting example embodiments include one or more fluorophores selected from dansyl aziridine, 4-chloro-7-sulfobenzofuran (SBF), 7-fluorobenz-2-oxa-1,3-diazole-4-sulfonyl fluoride (ABD-F) and nitrobenzoxadiazolyl. According to example embodiments fluorophores may include one or more of the following: fluoresceins such as fluorescein isothiocyanate, rhodamines such as rhodamine iodoacetamide, CY3 iodoacetamide and Green Fluorescent Protein, coumarins, 5-TMRIA (tetramethylrhodamine-5-iodoacetamide), o-aminobenzoic acid (ABZ), 5- or 5(6)-carboxyfluorescein (FAM), 5- or 5(6)carboxytetramethylrhodamine (TMR), 5-(2-aminoethylamino)-1-naphthalenesulfonic acid (EDANS), Quantum Red™, Texas Red™, Cy3™, 7-nitro-4-benzofurazanyl (NBD), N-((2-iodoacetoxy)ethyl)-N-methyl)am-ino-7-nitrobenzoxadiazole (IANBD), 6-acryloyl-2-dimethylaminonaphthalene (acrylodan), pyrene, Lucifer Yellow, Cy5™, Dapoxyl® (2-bromoacetamidoethyl)sulfonamide, (N-(4,4-difluoro-1,3,5,7-tetramethyl-4-bora-3a,4a-diaza-s-indacene-2-yl)-iodoacetamide (Bodipy® 507/545 IA), N-(4,4-difluoro-5,7-diphenyl-4-bora-3a,4a-diaza-s-indacene-3-propionyl)-N-'-iodoacetylethylenediamine (BODIPY® 530/550 IA), 5-((((2-iodoacetyl)amino)ethyl)amino) naphthalene-1-sulfonic acid (1,5-IAEDANS), carboxy-X-rhodamine, 5/6-iodoacetamide (XRIA 5,6), eosin, acridine orange, Alexa Fluor 350™, Alexa Fluor 405™, Alexa Fluor 430™, Alexa Fluor 488™, Alexa Fluor 500™, Alexa Fluor 514™, Alexa Fluor 532™, Alexa Fluor 546™, Alexa Fluor 555™, Alexa Fluor 568™, Alexa Fluor 594™, Alexa Fluor 610™, Alexa Fluor 633™, Alexa Fluor 635™, Alexa Fluor 647™, Alexa Fluor 660™, Alexa Fluor 680™, Alexa Fluor 700™, and Alexa Fluor 750™. Various photoluminescent labels that may be used in accordance with the present invention are also set forth in U.S. Pat. No. 6,197,258, which is incorporated herein in its entirety.

Other luminescent labeling moieties may include lanthanides such as europium (Eu3+) and terbium (Tb3+), as well as metal-ligand complexes of ruthenium [Ru(I)], rhenium [Re(I)], or osmium [Os(II)], typically in complexes with diimine ligands such as phenanthroline or bipyridyl.

Devices or sensor devices of the present invention may be made of any suitable material including for example, plastic, metal, glass and/or fused silica. By way of non-limiting example sensor devices may include one or more materials such as PTFE, polycarbonate, plasma-treated polystyrene, modified metal surfaces (e.g., thiolated gold), and the like. The material may be selected based on various factors including the selection of the binding entity, the sample, and/or the analyte to be determined. Other factors that may be relevant to the selection of the material may include for example contamination or cleaning considerations, mechanical stability, rigidity, machinability or ease of fabrication, and optical considerations including low intrinsic fluorescence or transparency.

Devices herein may be of any suitable shape for the embodiments described herein. For example, according to non-limiting example embodiments, devices may have at least one substantially planar side having a hole in which the binding entity is immobilized, in contrast to the rod-shaped fiber optic waveguides typically found in immunofluorescent assay devices. By way of further example, looking at the substantially planar side, example embodiments may be essentially disk-shaped, or essentially oval or square.

Binding entities or domains may be immobilized directly onto or into a matrix, such as a gel, bead or any other means for entrapping a binding entity known to those skilled in the art. By way of non-limiting example, a binding entity may be immobilized in hydrogel or sol-gel. Immobilization may include for example, where binding entities are physically entrapped in and surrounded by e.g., hydrogel, or where binding entities are covalently attached to and surrounded by e.g., hydrogel. As used herein, the term "matrix" may be any two dimensional or three-dimensional structure that is permeable to an analyte. The matrix may optionally prevent substantial interference from other molecules in a sample. According to example embodiments, the matrix may allow the binding protein to retain some degree of conformational and/or orientational mobility. Also according to example embodiments, a matrix may permit light from optical sources to pass through the sensor. According to example embodiments, the matrix additionally prevents or reduces leaching of the binding entity. The matrix may include multiple layers, for example with an inner layer serving to retain a binding protein, and one or more outer layers to control permeability. A "matrix" can be in any desirable form or shape including a disk, cylinder, patch, microsphere, porous polymer, open cell foam or the like, providing it is permeable to a target analyte.

According to example embodiments, hydrogels may include polysaccharides such as agarose, dextran, carrageenan, alginic acid, starch, cellulose, or derivatives of these such as, e.g., carboxymethyl derivatives, or water-swellable organic polymers such as, e.g., polyvinyl alcohol, polyacrylic acid, polyacrylamide, polyethylene glycol, poly-hydroxymethymethacrylate, copolymers of styrene and maleic anhydride, polyurethanes, copolymers of vinyl ether and maleic anhydride and derivatives thereof. In particular, non-limiting examples may include poly(ethylene glycol), poly(acrylamide), poly(acrylates) and/or tetraalkylammonium.

Sol-gels that may be useful may include material prepared by conventional, well-known sol-gel methods and may include inorganic material, organic material or mixed organic/inorganic material. The materials used to produce a sol-gel can include, but are not limited to, aluminates, aluminosilicates and titanates. These materials may be augmented with the organically modified silicates (Ormosils) and functionalized siloxanes, to provide an avenue for imparting and manipulating hydrophilicity and hydrophobicity, ionic charge, covalent attachment of protein, and the like. The term "sol-gel" is also intended to encompass modified "sol-gels".

According to example embodiments, covalent coupling of a binding entity to the matrix, such as a hydrogel, can take place after hydrogel formation or during hydrogel formation. For example, the polymer and the binding entity can be mixed with a crosslinking component, used in the formation of a hydrogel, in the presence of water to form the hydrogel sensor device in a single or "one pot" process.

The binding entity can also be covalently coupled to a preformed cross-linked matrix through site specific coupling. For example, when the binding molecule is a protein, site specific coupling to the hydrogel may be provided using free thiol groups at cysteine sites of the protein. By site-specific attachment, a binding protein can be covalently attached to the hydrogel while maintaining conformational freedom and analyte binding capability.

In example embodiments of an entrapment process, one or more hydrogels in water may be added to a binding protein in an aqueous buffer solution. Subsequent curing of the matrix, for example crosslinking, provides physical form. Using this technique and a conventional fabrication process (e.g. block casting, reverse emulsion polymerization, screen or contact printing, fluid-bed coating and dip or spin coating) one can obtain matrices in various configurations (e.g., granulates, nanoparticles, microparticles, monoliths, and thick and thin films).

In other embodiments, binding proteins may be physically entrapped or encapsulated within the aforementioned matrices, such as, but not limited to, the aforementioned hydrogels. Such methods of physically entrapping binding molecules include one and two pot methods previously described herein, without the coupling reaction between the binding entity and components of the matrix. In a specific embodiment, the physically entrapped or encapsulated binding protein hydrogel sensor device can be prepared in sheet form or deposited on a sheet that is capable of being subsequently cut into strips e.g., for in vitro use.

In example embodiments, a matrix, such as a hydrogel, may further comprise one or more additives. For example, one or more additives that may be included in the matrix include, but are not limited to, carbohydrates such as monosaccharides, disaccharides, polysaccharides, amino acids, oligopeptides, polypeptides, proteoglycans, glycoprotein, nucleic acids, oligonucleotides, lipids, fatty acids, natural or synthetic polymers, small molecular weight compounds such as antibiotics, drugs or drug candidates, and derivatives thereof. In example embodiments, the hydrogel sensors devices further include at least one carbohydrate or alcohol derivative thereof. More particularly, the hydrogel sensor devices may include at least one compound selected from the group consisting of allose, altrose, glucose, mannose, gulose, idose, galactose, talose, ribulose, fructose, sorbose, tagatose, sucrose, lactose, maltose, isomaltose, cellobiose, trehalose, mannitol, sorbitol, xylitol, maltitol, dextrose, and lactitol. Such additives can provide enhanced storage stability of a binding molecule in a hydrogel.

Covalent attachment of a binding entity to a matrix, such as a hydrogel, can also be accomplished via photo polymerization and crosslinking either concurrently or subsequently to formation of the matrix. The photo polymerization and crosslinking of the polymer to binding molecule may include the use of photoinitiators that generate reactive species, such as free radicals or cationic centers, upon exposure to an energy source. Examples of photoinitiators that may be used include, but are not limited to, peroxides, ketones, and azo compounds. Specific examples of photoinitiators include, but are not limited to, 2-hydroxy-2-methylpropiophenone, benzoin, and 2,2-dimethoxy-2-phenyl-acetophenone, and the like. The energy from the energy source may be from anywhere in the electromagnetic spectrum, such as, but not limited to, radio waves, infrared light, visible light, ultraviolet light, X-rays and gamma rays. In example embodiments, the energy source used to polymerize and crosslink a binding protein to a hydrogel is ultraviolet light.

Example devices may be able to convey a signal to a detector that can detect the signal and "quantify" the analyte. "Quantifying" analyte may include for example using optical methods such as fluorometric methods to analyze the analyte. The generated signal may be a direct indication of the binding of at least one target analyte to the binding entity on a device. The binding of the target analyte(s) to the binding entity either creates or alters the quality of a signal that is discernable using a detector. Changes in signal quality may include, but are not limited to, light wavelength shift and signal intensity. Different properties such as pH or concentration may be measured by the detector and/or calculated using for example, fluorescence intensity, intensity ratio, lifetime, or anisotropy (polarization). Photoluminescence lifetime may be measured by phase fluorometry, time-correlated-single photon counting, boxcar integration and time dependent decay. In some embodiments, the binding entities do not generate a signal when not bound to the target analytes. In other embodiments, the binding entities generate a signal, even when not bound to a target analyte, but the binding of the target analyte changes the quality of the signal, such that binding is discernable. According to other embodiments, it is also possible that the binding of a target analyte to the binding entity may cause a decrease in signal intensity, which alteration in the signal may be discernable to the detector.

Numerous fluorometric methods for the analysis of analytes, such as metal ions in solution are known and vary primarily in terms of signal transduction. Metal ion concentrations may be transduced as changes in fluorescence intensity or as changes in the ratios of fluorescence intensities at different wavelengths, as changes in fluorescence anisotropy (polarizations), or as changes in fluorescence lifetimes.

As used herein, the term "concentration" is used as it is in the art. A concentration may be expressed as a qualitative value, or more likely as a quantitative value. As used herein, the quantification of analytes can be a relative or absolute quantity. The quantity (e.g., concentration) of any of the analyte may be zero, indicating the absence of a particular analyte. The quantity may simply be the measured signal, e.g., fluorescence, without any additional measurements or manipulations. Alternatively, the quantity may be expressed as a difference, percentage or ratio of the measured value of the particular analyte to a measured value of another compound including, but not limited to, a standard or another analyte. The difference may be negative, indicating a decrease in the amount of measured analyte(s). The quantities may also be expressed as a difference or ratio of the analyte(s) to itself, measured at a different point in time. The quantities of analytes may be determined directly from a generated signal, or the generated signal may be used in an algorithm, with the algorithm designed to correlate the value of the generated signals to the quantity of analyte(s) in the sample.

Binding entities or domains may or may not correspond to the number of target analytes in a one to one fashion. For example, according to some embodiments, a sensor device may have only one type of binding entity per target analyte. In other embodiments, the sensor device may include more than one type of binding domain per target analyte.

"Photoluminescence," refers to any of a group of processes whereby a material is excited by radiation such as light, raised to an excited electronic or vibronic state, and subsequently re-emits that excitation energy as a photon of light. These processes include "fluorescence," which denotes emission accompanying descent from an excited state with paired electrons (a "singlet" state) or unpaired electrons (a "triplet" state) to a lower state with the same multiplicity; a quantum-mechanically "allowed" transition. Photoluminescence also includes phosphorescence, which denotes emission accompanying descent from an excited triplet or singlet state to a lower state of different multiplicity; a quantum mechanically "forbidden" transition. Compared to "allowed" transitions, "forbidden" transitions are associated with relatively longer excited state lifetimes. Photoluminescence also includes Raman scattering, where the wavelength of scattered light differs from that of the exciting light due to coupling with rotational, bending, or vibrational modes of molecules in the sample.

As indicated above, example devices herein may be able to convey a signal to a detector that can detect the signal and "quantify" the analyte. In example embodiments, the optical system/detector may be a device to detect or quantify light itself: such as a photomultiplier tube, photodiode, charge-coupled device (CCD), charge-injection device (CID), avalanche photodiodes, photographic film, the naked eye, and the like.

An "optical system" may include of a combination of one or more excitation sources and one or more detectors. It may also include filters, dichroic elements, a power supply, and/or electronics for signal detection and modulation. The optical system may optionally include a microprocessor. Example optical systems may provide a chassis or other means for mounting a device substantially at a focal point of an objective lens of the optical system. An "optical chassis" is a track of sorts that permits movement in at least one plane of a sensor device (e.g., where the sensor is in a holder that is adapted to move along the track) so as to position the sensor device at a desired location (e.g., at or near a focal point) in an optical system.

Sensor Devices

Example embodiments are generally directed sensor devices having at least one binding entity immobilized thereon, for example on a substrate or surface thereof, where binding entity is capable of generating a detectable signal upon binding of a target analyte thereto. As discussed further herein, the binding entity may be entrapped for example in a gel or on beads immobilized on the sensor device. The sensor device is adapted such that it is capable of being mounted in an optical system to detect, measure and/or quantify the detectable signal. Optionally, the sensor device is adapted such that it is capable of being removably mounted in an optical mount, e.g., via an optical chassis, to the optical system. According to example embodiments, the binding entity may be reversibly bound to the target analyte.

According to further example embodiments, the target analyte is a metal ion. In particular, examples of metal ions that may be detected may include at least one metal ion selected from Zn(II), Cu(II), Cd(II), Co(II), Ni(II), Fe(II), Mn(II), Pb(II), and Hg(II).

According to example embodiments, the binding entity may include at least one macromolecule and at least one photoluminescent label, such as a fluorescent marker. According to example embodiments, the macromolecule may include one or more molecules selected from apocarbonic anhydrase, phosphatase, leucine aminopeptidase, carboxypeptidases, laccases, azurins, ureases, and mutants and variants thereof. The photoluminescent label may be adapted to undergo a luminescent change upon binding of the target analyte to the macromolecule.

The binding entity may be entrapped for example in a gel or on beads immobilized on the sensor device. The binding entity may be entrapped for example in a hydrogel, sol-gel, or polyacrylamide or other material that may allow small molecules (i.e., the analyte) to diffuse readily through the material, such that they may contact and bind with the binding entity. Binding protein may be placed for example in a small hole in a disk-shaped substrate. The hole may be for example a few hundred microns in depth and width. A gel or other material entrapping the binding protein may be polymerized within a polymer sensor device.

According to example embodiments the sensor device may include one or more materials such as plastic, fused silica, metal or glass. In particular, when a metal ion is a target analyte the sensor device may include PTFE, polycarbonate, plasma-treated polystyrene, or other polymers. Such polymers may be advantageous in that they may be readily acid cleaned to reduce or avoid contamination and contain little in the way of contaminant analytes or interferents. Other sensor device materials, such as a metal may be suitable depending on the target analyte(s) and/or binding entity.

According to example embodiments, a sensor device may include more than one type of binding entity or more than one binding site on a binding entity, suitable for binding one or more target analytes in the sample. Each binding entity may be capable of binding a different target analyte. In embodiments having more than one binding entity, the types of binding entities may be substantially segregated and immobilized onto different portions of the sensor device to allow each target analyte to be determined separately from one another (either simultaneously or sequentially). For example, an excitation source may first be directed to a first portion of the sensor device having one type of binding entity and therefore one type of analyte bound thereto; and thereafter the excitation source may be directed to a second portion of the sensor device having a second binding entity and a second analyte bound thereto.

Example embodiments may include immobilizing a relatively small amount of binding entity on the sensor device. In the case of multiple types of binding entities, example embodiments may include a relatively small amount of each type of binding entity on the sensor device. For example, each binding entity immobilized on the sensor device may be present in an amount of less than one picomole.

Figure 8:
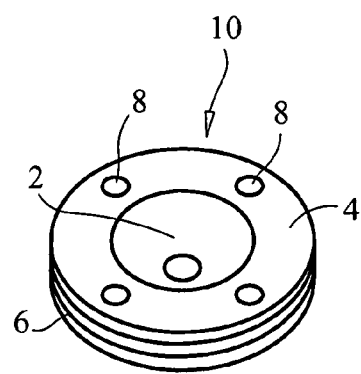
FIG. 8 depicts example mounting devices of FIGS. 1A-1C.
Figure 9C:
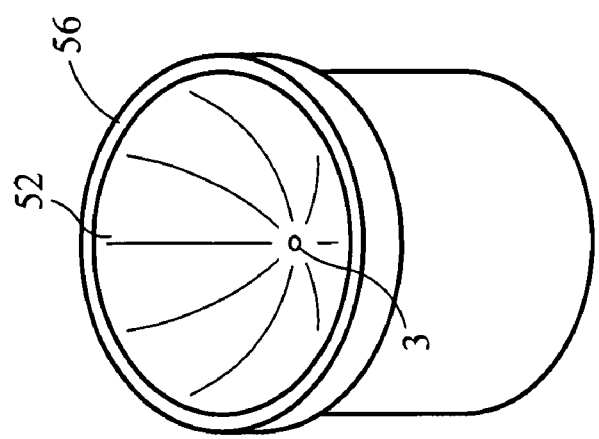
FIGS. 9A, 9B and 9C depict sensor devices according to non-limiting example embodiments.
Figure 9B:
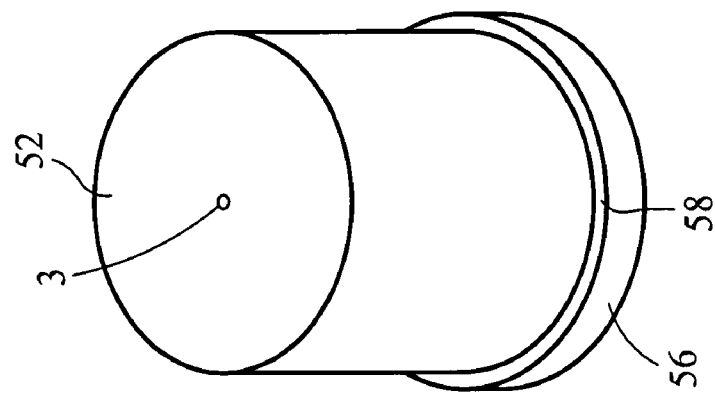
Figure 9A:
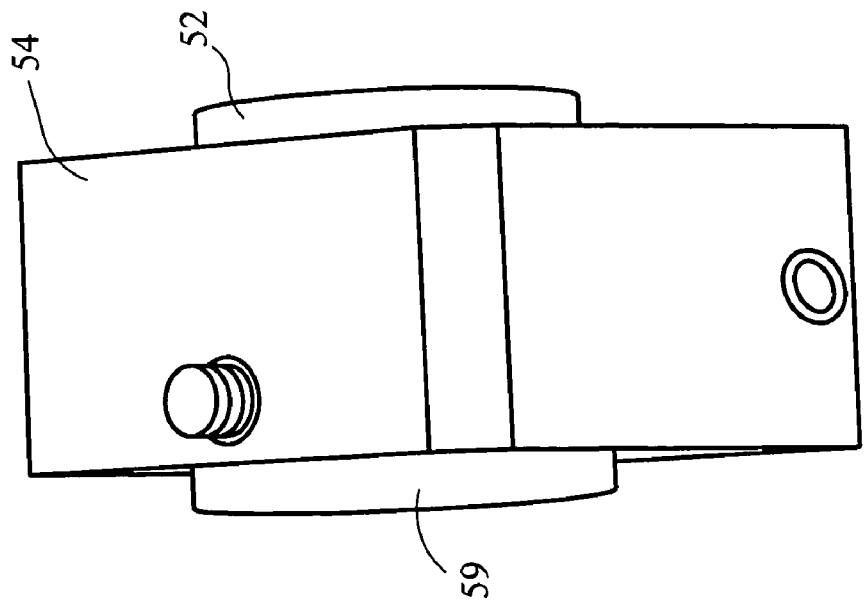
Figure 10C:
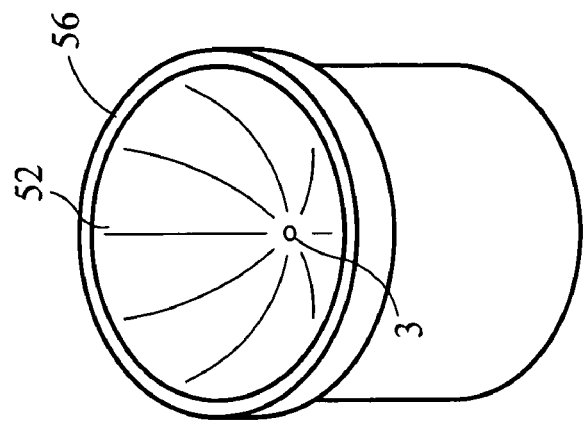
FIGS. 10A, 10B and 10C depict sensor devices according to non-limiting example embodiments.
Figure 10B:
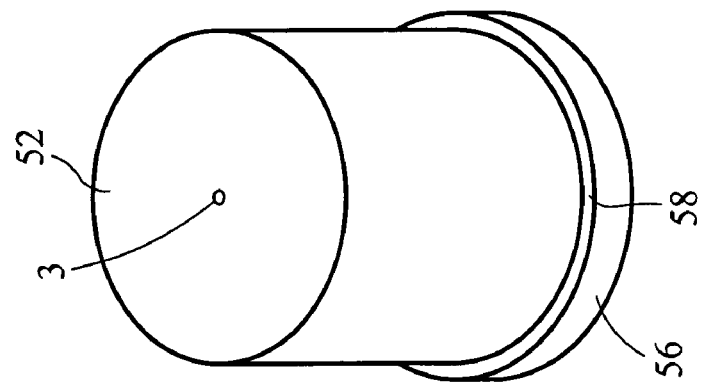
Figure 10A:
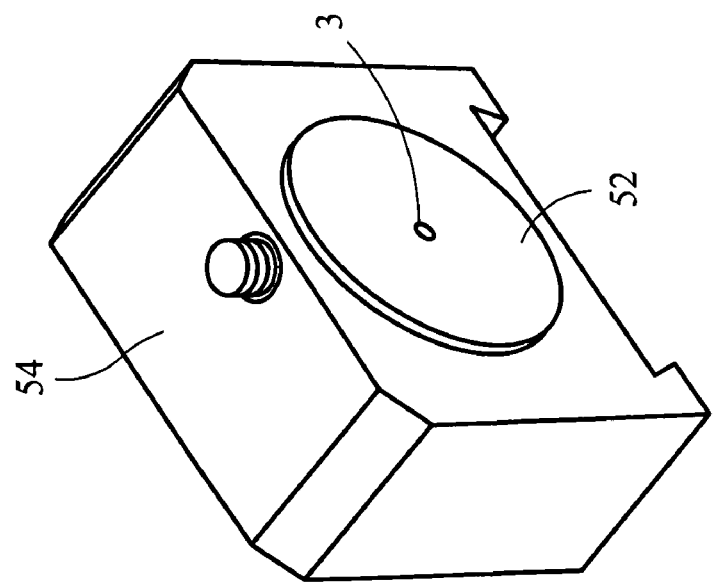

FIGS. 1A, 1B and 1C depict back, side/back view, and cross-sectional views, respectively of an example sensor device. According to the embodiments depicted in FIGS. 1A, 1B and 1C, one type of binding entity is located toward the center of a substrate 4 of the sensor device. In particular, by way of non-limiting example, a binding entity such as CA II may be entrapped and concentrated in a droplet of hydrogel polymerized in situ toward the center 2 of the substrate 4. According to example embodiments, a binding element may be included substantially at a cylindrical voxel 3, such that the binding element (e.g., hydrogel) may be positioned substantially at the vertex of a conical or biconical beam path from the objective in an optical system. The angle of a conical opening in the sensor device may then be determined by the numerical aperture (or focusing angle of the objective). FIG. 8 further depicts sensor devices in accordance with these examples.

Although the sensor device is depicted in FIGS. 1A and 1B as being substantially disk-shaped, other shapes may also be suitable. According to the example depicted in FIGS. 1A and 1B, the side 6 of the sensor device may include RMS screw threads, which as described further below, may enable the sensor device to be mounted e.g., in a sensor device holder or optical mount. Alternatively, other methods of mounting may be used, such as other forms of screwing, bayonet mounting, friction locking, breach locking the sensor device, and/or by other methods available to those skilled in the art. Holes 8 may be present in any desired location for use of a tool to assist in mounting the sensor device e.g., in a sensor device holder or optical mount for mounting the sensor device to an optical system, without risking contamination of the binding entity or analyte bound thereto. Holes 8 may not be necessary in other embodiments, depending for example on the mounting method to be used.

FIGS. 9A-9C and 10A-10C depict other example embodiments of sensor devices. According to these examples, a sensor device 52 may be designed such that it is capable of fitting in a mount 54, such as a 561-FCA mount (Newport Corporation). Sensor device 52 may include a flange 56 or other design feature to assist in positioning the sensor device within the mount 54. According to the examples depicted in FIGS. 9A-9C and 10A-10C, the sensor device 52 is inserted into the mount 54 until the face 58 of the flange 56 hits the face of the mount. The sensor device may be designed to maintain its position within a mount, for example by fitting snuggly within the mount or by a set screw or other means. Alignment tools according to these embodiments may be made for example out of aluminum, such that impact of the exciting beam on the walls of the hole may be discernable by the reflection.

As depicted in FIGS. 9A-9C and 10A-10C, the sensor devices depicted therein (similar to the embodiments of FIGS. 1A, 1B and 1C), have a substantially conical opening 68 (see FIGS. 11A and 11B), and a binding element may be included substantially at a cylindrical voxel 3, such that the binding element may be positioned substantially at the vertex of a conical or bioconical beam path from the objective in an optical system. The angle of the conical opening may then be determined by the numerical aperture (or focusing angle of the objective).

FIGS. 11A and 11B depict side and front views, respectively, of the sensor device depicted in FIGS. 9A-9C and 10A-10C. According to non-limiting example embodiments, a beam may be focused on the center of a relatively small diameter (e.g., 0.5 mm), short depth (e.g., 1 mm) hole 3 of the example device. In these examples, the volume of the hole containing the entrapped binding entity may be approximately 0.2 microliters, may be convenient, and the relatively large size of the hole diameter may make alignment comparatively easier than for a fiber optic. These example measurements and dimensions are not limiting however, and may be varied. For example, in some embodiments where the sensor device may be used to analyze smaller samples or those with less analyte, the diameter of the hole and its length can be at least ten-fold smaller. The dimensions can be larger as well.

FIGS. 11A and 11B also depict a potential location of an optional hole 70, which may be present in the sensor devices described herein. One or more optional holes may be useful for example with respect to holding the device e.g., to facilitate its transfer into a mount, or contact a device with a sample. According to non-limiting embodiments, hole 3 in FIG. 11B is at the near end looking down the optical axis.

Figure 12:
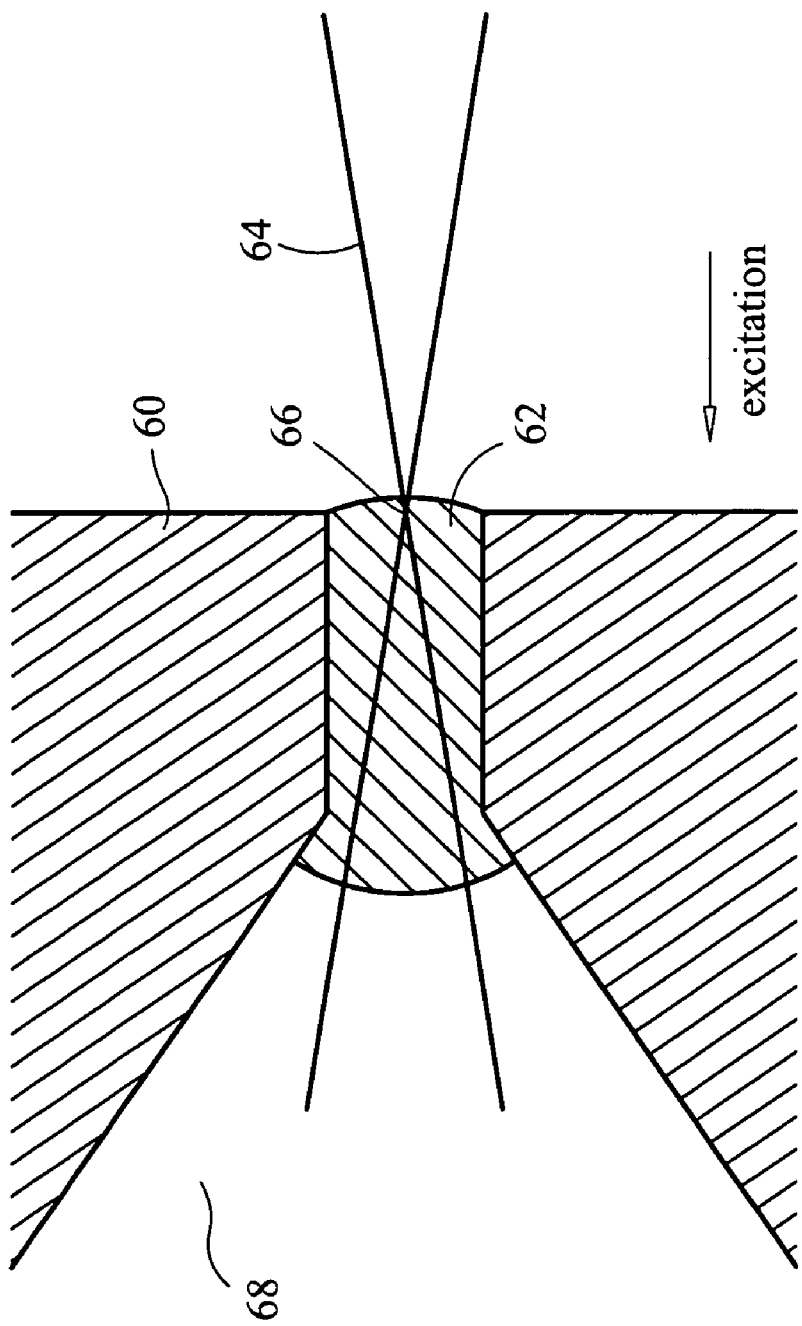
FIG. 12 depicts a close up cross-section of an example sensor device.

FIG. 12 depicts a cross-section of an example sensor device 60 having a binding entity immobilized thereon, in this case by being entrapped for example in a hydrogel 62 in a cylindrical voxel opening of the sensor device. As depicted in FIG. 12, an exciting beam 64 may be focused 66 at a point in the entrapped binding entity within a cylindrical voxel opening. According to these embodiments, the beam is focused substantially at the center of a hole in the sensor device and excites fluorescence in the hydrogel (or other entrapping substance) containing the binding entity. According to non-limiting example embodiments, the beam may be focused on the center of a small diameter (e.g., 0.5 mm), short depth (e.g., 1 mm) hole. The fluorescence excited is collected for example on the side from whence the excitation came. A conical opening 68 in the back side of the sensor device may have a broad enough angle such that the excitation beam strikes essentially only the hydrogel (or other entrapping substance) containing the binding entity. The angle of the excitation beam can be predicted from the numerical aperture (or beam size and focal length) of the objective being used to focus it.

According to alternative example devices, sensor devices need not include a conical opening and they need only be a thickness corresponding to the depth of the hole (e.g., 1 mm). In these embodiments, the devices may be more disc-like, which may result in them being less mechanically stable and more difficult to mount. If the depth of the hole is greater (e.g., several mm, corresponding to the length of the sensor device along the optical axis), but there is no conical opening, the exciting beam will strike the walls of the hole, potentially causing backscatter, which can corrupt the measurements. In addition, the binding entity throughout the gel will come to equilibrium much more slowly because the analyte must diffuse through a longer length of gel.

Although example sensor devices have been discussed, many other embodiments may be used for mounting the entrapped binding entity substantially at a focus of an exciting beam so as to minimize the amount of scattered excitation. The examples discussed herein are convenient and offer advantages, but are not meant to be limiting.

Methods of Quantifying an Analyte

Example embodiments are also generally directed to methods that include contacting a sensor device with a sample containing at least one target analyte; allowing the target analyte to bind with at least one binding entity immobilized on the sensor device; mounting the sensor device in an optical mount; and quantifying analyte in the sample.

Contacting the sensor with the sample may include mounting the sensor device into a sensor device holder and inserting the sensor device holder into a container having the sample therein. Either the sample may be in the container before the sensor device is inserted therein or sample may be added to the container after insertion of the sensor device. According to example embodiments the sensor device may be adapted such that it may be mounted in a sensor device holder.

According to example embodiments, the sensor device 10 may be mounted in the sensor device holder by a method selected from screwing, bayonet mounting, friction locking or breach locking the sensor device into the sensor device holder, and/or by other methods available to those skilled in the art. In an example of screwing, the sensor device and the holder may each be adapted for example with a Royal Microscopical Society (RMS) screw thread such that the sensor device may be screwed into the holder. Similarly, an optical mount in an optical system such as an objective holder 12 shown in FIGS. 2A and 3 may be adapted with an RMS screw thread, so that the sensor device may be screwed in and out of an objective holder also. If bayonet mounting is used to mount the sensor device in a device holder, bayonet mounting may be used to connect the sensor device to an optical mount.

Screwing, or other methods of mounting a sensor device, e.g., into a sensor device holder or optical mount (such as an objective holder or an optical fiber connector) may be aided for example using a tool that allows one to control the sensor device holder and/or mount. Such a tool may minimize any potential contamination that may occur e.g., by handling the sensor device. According to example embodiments, the sensor device may be adapted to include one or more indentations, holes, and the like into which a tool may be inserted or tabs or other projections that may aid a tool in mounting the sensor device.

The container may include for example a bottle, such as a Nalgene plastic bottle or other commonly used containers for holding a sample containing an analyte.

Allowing the target analyte to bind with binding entity may include allowing the sufficient time for the binding reaction to substantially equilibrate, thus, allowing for maximum or nearly maximum (e.g., 90%) binding that would take place at equilibrium, which may depend e.g., on the particular binding entity, analyte, binding constant, sample, etc. . . .

The sensor device may be mounted in an optical system by several methods, which preferably allow for the sensor device to by reproducibly and precisely (e.g., to within 50 micrometers or less) mounted at a specific location of the optical system. For example, as shown in FIGS. 2A and 3, the sensor device 10 may be mounted in an optical mount, such as an objective holder 12, which according to example embodiments may be positioned substantially at the focal point (e.g., within 50 micrometers or less from the focal point) of an objective lens 14 in an optical system for example by mounting the mount in an optical chassis 16. The mount may be, for example, any mechanical device, such as standard fiber optic connectors, luer locks, plastic, metal, or glass sleeves, or spring-loaded housings. The mount may be adapted such that a sensor device may be mounted therein, for example by screwing, bayonet mounting or friction locking. The mount may be a standard objective holder known in the art, such as a Newport 561-OBJ, or it may include a fiber optic connector (such as a modified SC connector), or any objective holder or adapter such as 561-FCA (Newport Corporation) adapted to mount a sensor device therein.

A purpose of the optical mount may be to provide a component that allows the other components (such as devices described herein) to be readily detachable so that the devices are interchangeable and may replaceable. Thus, various sensor devices may be interchangeably inserted and removed from such a mount, while the mount remains substantially in place. According to example embodiments, the sensor device may be removably mounted in a mount, e.g., by screwing. It may be useful for example, to mount a first sensor device in a mount such as an objective holder, determine a first analyte concentration in the fluorometer, and without removing the mount from the optical system, dismount the first sensor device and mount a second sensor device to determine a second analyte concentration. Such a method may allow one to quickly evaluate multiple analytes from multiple devices that were in contact with multiple samples, without needing to worry about positioning the sensor device in the fluorometer. The stationary mount would allow the position of each device to be reproducible. In example embodiments, the mount may be a fiber optic connector that may be used to allow fiber optic probes or sensor devices described herein to be interchangeably mounted in the optical system without having to reposition the mount, thus, decreasing potential variations and inaccuracies caused by moving the mount and/or sensor location on the optical system.

In alternative embodiments, a sensor device may be inserted into a mount when the mount is detached from the optical system, and then the mount may be mounted in the optical system. According to additional example embodiments, a sensor device may be removed from the mount after the mount is removed from the optical system.

Quantifying analyte in a sample may include for example providing energy to the sensor device, where the sensor device (mounted in an optical mount) is positioned substantially at a focal point of light passing through an objective lens in an optical system, and measuring a detectable signal emitted by the binding entity bound to the target analyte when the sensor device receives energy. In particular, according to example embodiments, the fractional occupancy (and analyte concentration) may be read by measuring luminescence intensity, intensity ratio, or anisotropy (polarization).

The present sensor devices may be used to analyze multiple samples, for example, in parallel. In particular, it may take several hours or days for the binding entity on a sensor device to equilibrate with a target analyte in a sample. Thus, multiple sensor devices may be exposed to multiple samples in separate containers substantially concurrently so the equilibration of the binding protein on each sensor device with analyte in its respective sample, can take place substantially in parallel. Each sensor device may then be mounted into the optical system to measure the analyte in each sample.

Optical Systems

An "optical system" may include of a combination of one or more excitation sources and one or more detectors. It may also include filters, dichroic elements, a power supply, and/or electronics for signal detection and modulation. The optical system may optionally include a microprocessor. Example optical systems may provide a chassis or other means for mounting a device substantially at a focal point of an objective lens of the optical system.

According to example embodiments, an optical system may interrogate a device by coupling one or more excitation wavelengths of light and directing them to a sensor device to illuminate the sensor device. The binding of a target analyte to a binding entity may result in a particular wavelength, intensity, lifetime, energy transfer efficiency, and/or polarization of the luminescence of a luminescent label that may be part of the binding entity. A resulting luminescence signal may be detected, interpreted, and stored and/or displayed in the optical system. In certain embodiments, the optical system may include multiple excitation sources. One or more of these sources may be modulated to permit dynamic signal processing of the detected signal, thereby enhancing signal-to-noise and detection sensitivity.

Example embodiments include an optical system having a light source providing energy or light; an objective lens creating a focal point of light passing through the objective lens; a sensor device mounted substantially at the focal point; and a detector. The sensor device may include any of the devices herein. For example, the sensor device may include a surface having at least one binding entity immobilized thereon, for example, where a binding entity is entrapped in a gel on the sensor device. Each binding entity may include at least one binding site that selectively binds at least one target analyte, and the binding entity bound to a target analyte emits a detectable signal when the sensor device receives light. The detector may be positioned to detect the detectable signal. According to example embodiments, a sensor may be substantially planar on a side positioned to receive light from the light source.

Figure 4:
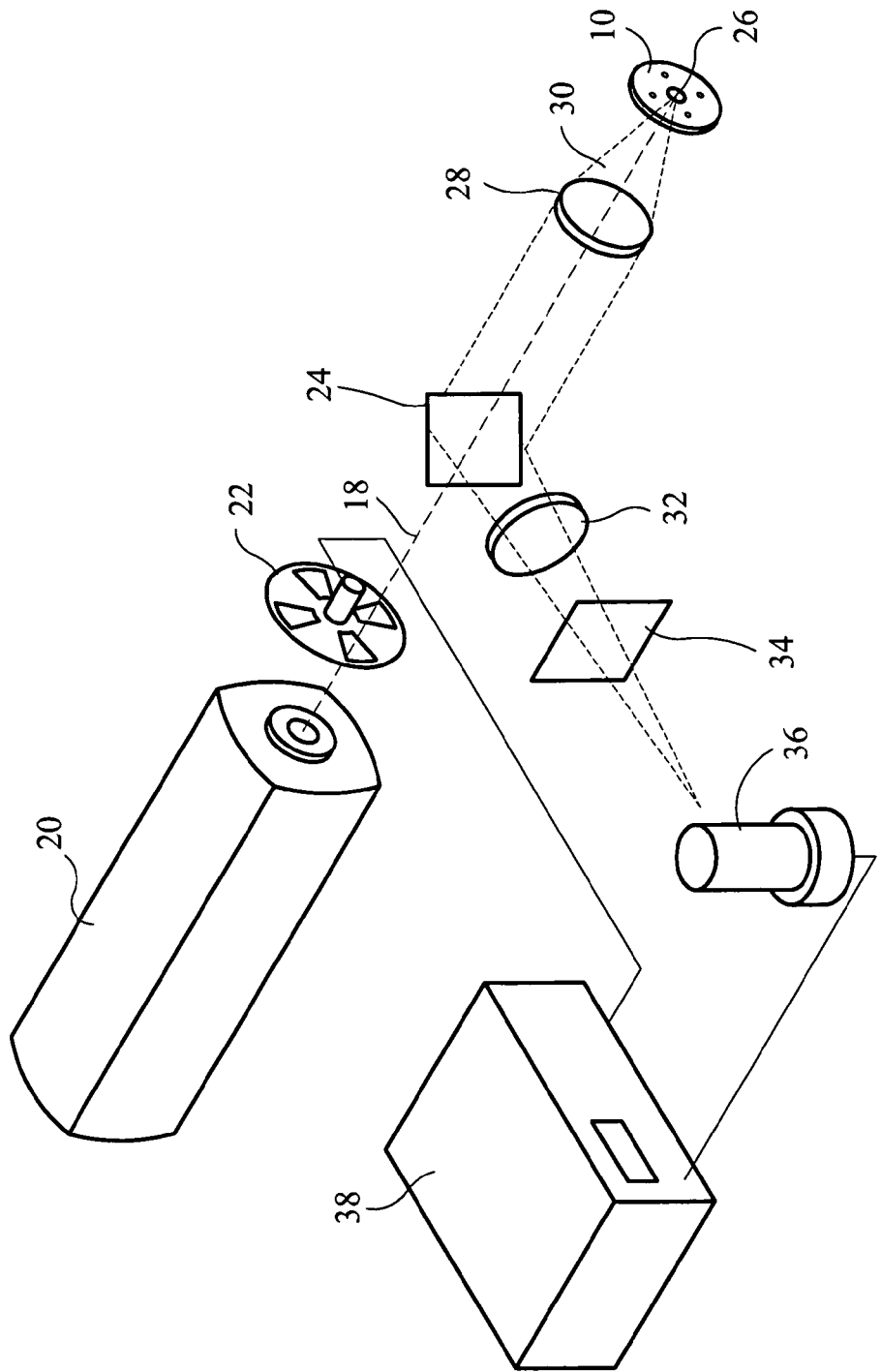
FIG. 4 depicts an example optical system in accordance with non-limiting example embodiments.

An example optical system configuration may be as depicted in FIG. 4. According to example embodiments the light source may be a laser. Ultraviolet excitation for example, may be useful for detecting many photoluminescent molecules. Excitation 18 from the laser 20 passes through a chopper 22 and a dichroic beamsplitter 24 to a sensing device 10 located substantially at the focal point 26 of a lens 28. The excitation excites a fluorescent label of a binding entity immobilized on the sensing device bound to a target analyte. Beam 30 reflects off the beamsplitter 24, through a lens 32 and a barrier filter 34 to a detector 36.

The chopper 22 may serve to modulate the excitation light at a select frequency. The use of a chopper or other light modulator together with a lock-in amplifier 38 or other phase-sensitive detector is well known in the art for improving the detectability of weak signals, such as in fiber optic sensors. Thus, a chopper 22 placed in the beam of exciting light will modulate it at a particular frequency, and the lock-in amplifier 38 can be tuned to measure the detector 36 output at only that frequency, eliminating spurious noise at other frequencies. The chopper 22 may be placed as closely to the light source 20 as is convenient.

The excitation/light source may be directed by mirrors to the sensor device. The number and arrangement of mirrors may be varied, as necessary, to accommodate various space limitations, so long as a sufficient amount of light is directed to the sensor device.

Many types of lenses or objectives may be used, including gradient index rod lenses, simple lenses, spherical lenses, and most often, refracting microscope objectives.

The purpose of the filter 34 in FIG. 4 is to block scattered exciting light from entering the detector 36 and being confused with authentic (signal) photoluminescence. Such scattered light can be orders of magnitude stronger than the actual photoluminescence, and can seriously degrade the performance of the sensor.

The detector 36 may be positioned to detect fluorescent light emitted from sensor device 10. The emitted light may be reflective of the concentration of a selected analyte in a sample. Many kinds of light detectors have been used to detect the photoluminescence signals. A suitable detector may be any type of photodetector useful to detect light in the wavelength region spanning the wavelength range of the emitted luminescence, as known in the art. For example, a detector may be a CCD (charge-coupled device) detector, a photomultiplier (such as photomultiplier tubes), a semiconductor photodiode, phototransistors, or an array of such detectors. With an array of small detectors, the user can determine that the peak photoluminescence is being detected and is not inadvertently missed due to misalignment of the collection and detection optics. The usefulness of a detector is mainly determined by their sensitivity.

According to example embodiments signal amplification and processing may be performed for example by an exemplary Stanford Research Systems (Sunnyvale, Calif. 94089) lock-in amplifier 38 connected to a chopper 22 from the same manufacturer.

Optical Mounts

Other example embodiments include an optical mount itself, which is adapted such that it is capable of being mounted to an optical system, where the mount is adapted to immobilize a sensor device therein. Thus, the mount may removably mount a sensor device to the optical system. The mount may be adapted such that it may position a sensor device mounted therein substantially at a focal point of an objective lens in an optical system.

Example embodiments also include systems that include a mount adapted to be capable of being mounted in an optical system; and a sensor device adapted such that it is capable of being mounted within the mount. The optical mount may be mounted in an optical system such that the sensor device is positioned substantially at a focal point of an objective lens.

Further example embodiments are directed to methods that include mounting a sensor device at substantially at a focal point of an objective lens in an optical system. The sensor may be mounted for example, within a mount, such as an objective holder or a fiber optic connector.

Sensor Device Holders

Example embodiments are also directed to sensor device holders that include a portion capable of immobilizing a sensor device, where the sensor device holder is adapted for insertion into a container. The sensor device holder may then be inserted into the container, allowing the sensor device to contact an analyte-containing sample in the container. Sensor device holders may be of any suitable shape or size that fits into a desired container.

Figure 5:
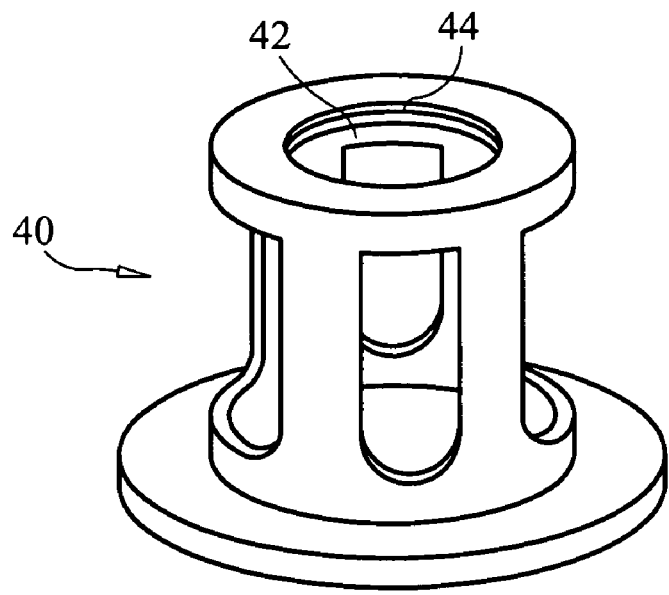
FIG. 5 depicts a sensor device holder in accordance with non-limiting example embodiments.
Figure 6:
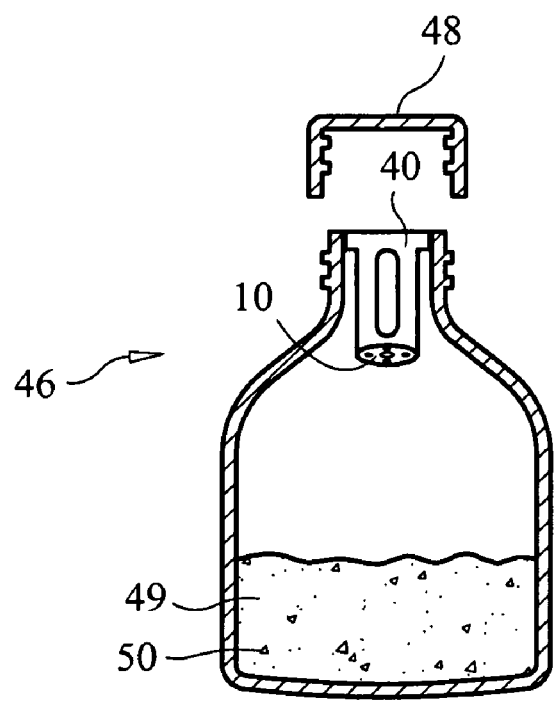
FIG. 6 depicts a bottle having analyte-containing sample therein, where the sensor device holder of FIG. 5 has been inserted into the bottle, in accordance with non-limiting example embodiments.
Figures 7A, 7B:
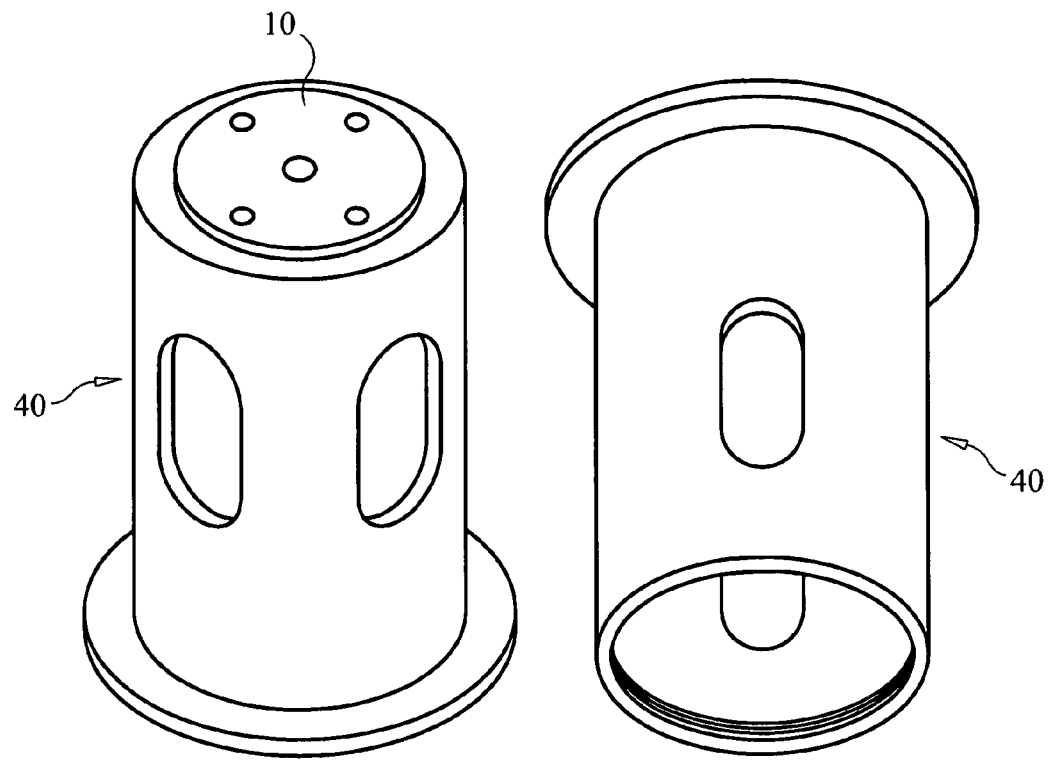
FIGS. 7A and 7B depict example sensor device holders, the holder of FIG. 7A having a sensor device mounted therein, and the holder of FIG. 7B not having a sensor device mounted therein, in accordance with non-limiting example embodiments.

By way of non-limiting example, a sensor device holder may be adapted for use with a standard bottle, such as a Nalgene bottle. FIGS. 5-7 depict non-limiting embodiments of an example sensor device holder and container for which such a holder may be adapted. As shown in FIG. 5, a sensor device holder 40 may be adapted such that it has a location 42 in which to immobilize a sensor device 10, and is adapted with screw threads 44, such that a sensor device fits into location 42 and may be immobilized by being screwed into the screw threads.

After insertion of the sensor device into the container, the container may be agitated or stirred if desired, until equilibration between the sensor device and the sample occurs (e.g., up to several hours). Then the device may be removed and mounted in an optical system e.g., by screwing the device into an optical mount According to example embodiments, the sensor device holder is further adapted such that when the holder is inserted into a container 46, the container lid 48 may fit over the holder. Thus, the lid may be engaged for example if shaking, tilting or inverting of the container is required for the sample 49 to contact the sensor device 10, allowing analyte 50 to contact the sensor device. Alternatively, the sensor device may be adapted such that it provides a sealed lid upon insertion, thus obviating the need for a separate container lid.

The sensor device and the holder may each be made of one or more of PTFE, polycarbonate, glass, fused silica, and/or other materials that can be readily acid-cleaned to avoid or reduce contamination.

Further example embodiments are directed to systems that include a sensor device, a sensor device holder and a container suitable for holding a sample, where the sample contains at least one target analyte.

Kits

Further included are kits that include devices described herein.

Example kits may include a sensor device, a container, and a sensor device holder capable of immobilizing the sensor device for insertion into the container. Such kits may further include one or more additional components, such as a tool for mounting the sensor device into the holder or removing it therefrom, instructions for use, a lid for the container, such as a screw top lid, which may be particularly useful when the container must be shaken, tilted or inverted for any sample in the container to contact the sensor device. The sensor device may be included in the kit either fully assembled (e.g., having a binding entity already immobilized thereon), or unassembled (e.g., where the user immobilizes one or more binding entities onto the sensor device). Where a sensor is included unassembled, one or more binding entities may be provided with the kit.

Other example kits may include a sensor device and a mount adapted such that it is capable of immobilizing the sensor device, and adapted such that it may be mounted in an optical system. Such kits may further include one or more additional components, such as a tool for mounting the sensor device into the holder or removing it therefrom. Kits may also include instructions or written material to aid a user. As with the previous embodiments, the sensor device may be provided assembled or unassembeled (where one or more binding entities are separately provided with the kit).

Methods to Determine a Rise in Concentration

Also included are methods that include contacting a device having at least one binding entity immobilized thereon, wherein the binding entity is capable of generating a detectable signal upon binding of a target analyte to the binding entity, with a sample containing the target analyte; determining analyte concentration from the detectable signal; and optionally repeating the contacting and determining one or more times to determine if the analyte concentration spikes or exceeds a predetermined level or to determine the maximum concentration from each of the determined concentrations. A spike in concentration, or reaching a predetermined concentration level (which may be a predetermined absolute level or increase over the starting concentration or previous measured concentrations such as an increase of 50% or more over the starting concentration), may trigger an alarm response. The recording of values or the alarm response may include any response to alert a reader as to the concentration spike or rise in level. For example, the alarm may be a light sound, computer message, beeper, text message, markings on paper, etc.

According to these example embodiments, sensor devices described herein may be used. Such a device may be contacted with a sample to allow analyte in the sample to bind to the binding entity immobilized on the sensor devices. Then, the sensor device may be mounted in an optical system for measurement of analyte concentration. Thereafter the sensor device may be reinserted into the sample such that analyte may again bind to the sensor device and another analyte concentration may be read at a later time. Although binding of the analyte to a binding entity is a reversible process, depending on the selection of the binding entity (for example if certain wild-type binding proteins are used), the process may not have time to completely reverse before the second and subsequent processes are started. Thus, in such a circumstance, these methods may be particularly useful for reading increasing concentrations of analyte levels. But after a spike or high analyte concentration is determined, the sensor device may need to be replaced, at least until the binding on the previous sensor has sufficiently reversed.

According to alternative embodiments of these methods, a fiber optic or other sensor may be used, for example in a situation where analyte concentrations are desired in the sea or some other inaccessible location. Such methods may provide for an alarm response in a case where a particular analyte concentration, rise in concentration, or spike is recorded.

Readings may be intermittent (either at regular intervals e.g., in an automated system or measured by a human periodically) or in the case of a fiber optic sensor, readings may be continuous.

The following examples illustrate non-limiting embodiments. The examples set forth herein are meant to be illustrative and should not in any way serve to limit the scope of the claims. As would be apparent to skilled artisans, various changes and modifications are possible and are contemplated and may be made by persons skilled in the art.

EXAMPLE 1

In this example, human apocarbonic anhydrase II variant L198C fluorescent labeled with Alexa Fluor 660 maleimide is entrapped at 1 µM within a sensor device in a polyacrylamide gel comprising 7% acrylamide monomer and 0.2% N,N-methylene bis acrylamide in pH 7.5 MOPS buffer. After contacting the sensor device with an aqueous sample such as sea water, the proportion of the protein with target analyte, Cu(II), bound in the active site is quantitated by measuring the proportion with a short (0.3 nsec) vs. unquenched (1.7 nsec) lifetime by mounting the sensor in a phase fluorometer configured as in FIG. 4, with a 655 nm diode laser excitation source and measuring the frequency-dependent phase and modulation through a 682DF22 emission filter. The proportion of protein with Cu(II) bound (and thus the free Cu(II) concentration to which the device was exposed) may also be measured by measuring the phase and modulation at a single modulation frequency ranging from approximately 60 MHz to 200 MHz and comparing them to those measured for the device in copper-buffered calibration standards, which are formulated using methods known in the art, as previously described (H. H. Zeng, et al., Analytical Chemistry, Vol. 75, pp. 6807-12 (2003), incorporated herein by reference).

Similarly, the free Cu(II) concentration to which the device has been exposed may also be measured by using as a binding agent such as apoF131C-ABD-T and exciting at 426 nm, measuring the polarization (also known as fluorescence anisotropy) of emission at 550 nm as described previously (R. B. Thompson, et al., Analytical Chemistry Vol. 70, pp. 4717-4723 (1998), incorporated herein by reference), and comparing it to the same measurement performed on Cu(II) buffers of known free Cu(II) concentration using methods well known in the art.

EXAMPLE 2

In this example, 5 µM apoH94N human CA II is coentrapped in a sensor device in a 7% polyacrylamide gel that is 10 mM MOPS pH 7.5 and 100 mM NaCl with 10 µM poly-ABD-N, and put in contact with an aqueous sample having a free zinc concentration of approximately 5 nanomolar. Polymeric ABD-N is a polymeric form of ABD-N made by condensation of polyamino dextran with ABD-F. The device is excited with an excitation source (such as a 408 nm diode laser) and the fluorescence intensities are measured though interference filters whose peak transmissions are approximately 550 nm and 600 nm, and their ratio determined. The free zinc ion concentration to which the device was exposed is measured by comparison with the same measurement performed on devices contacted with zinc solutions having known free zinc ion concentrations formulated by methods well known in the art (R. B. Thompson, et al., Journal of Neuroscience Methods Vol. 96, pages 35-45 (2000), incorporated herein by reference).

Similarly, apo-N67C-ABD-T may be entrapped in a sensor device in a polyacrylamide gel. The device may then be exposed to a sample and incorporated into a fluorometer as in FIG. 4, excited at 430 nm, its emission observed at a wavelength of 550 nm, and its fluorescence polarization measured as described previously (Thompson, et al., Anal Chem. 70, 4717 (1998), incorporated herein by reference). The concentration of free Zn(II) may be determined by comparison of the measured polarization (anisotropy) with standards of known free zinc ion concentration.

Similarly, apo-N67C-ABD may be used to determine free zinc ion if its fluorescence intensity, lifetime, or phase and modulation at a modulation frequency of approximately 101 MHz are measured when it is incorporated into a hydrogel in the device as described above, is excited at approximately 400 nm and its emission observed at 500 nm, and the intensity, lifetime, and or phase angle or modulation compared with the same parameter measured for the labeled binding agent having been exposed to a buffer of known free zinc concentration, as previously described (R. B. Thompson, et al., Analytical Biochemistry Vol. 267 pp. 185-195 (1999), incorporated herein by reference).

EXAMPLE 3

Figure 13:
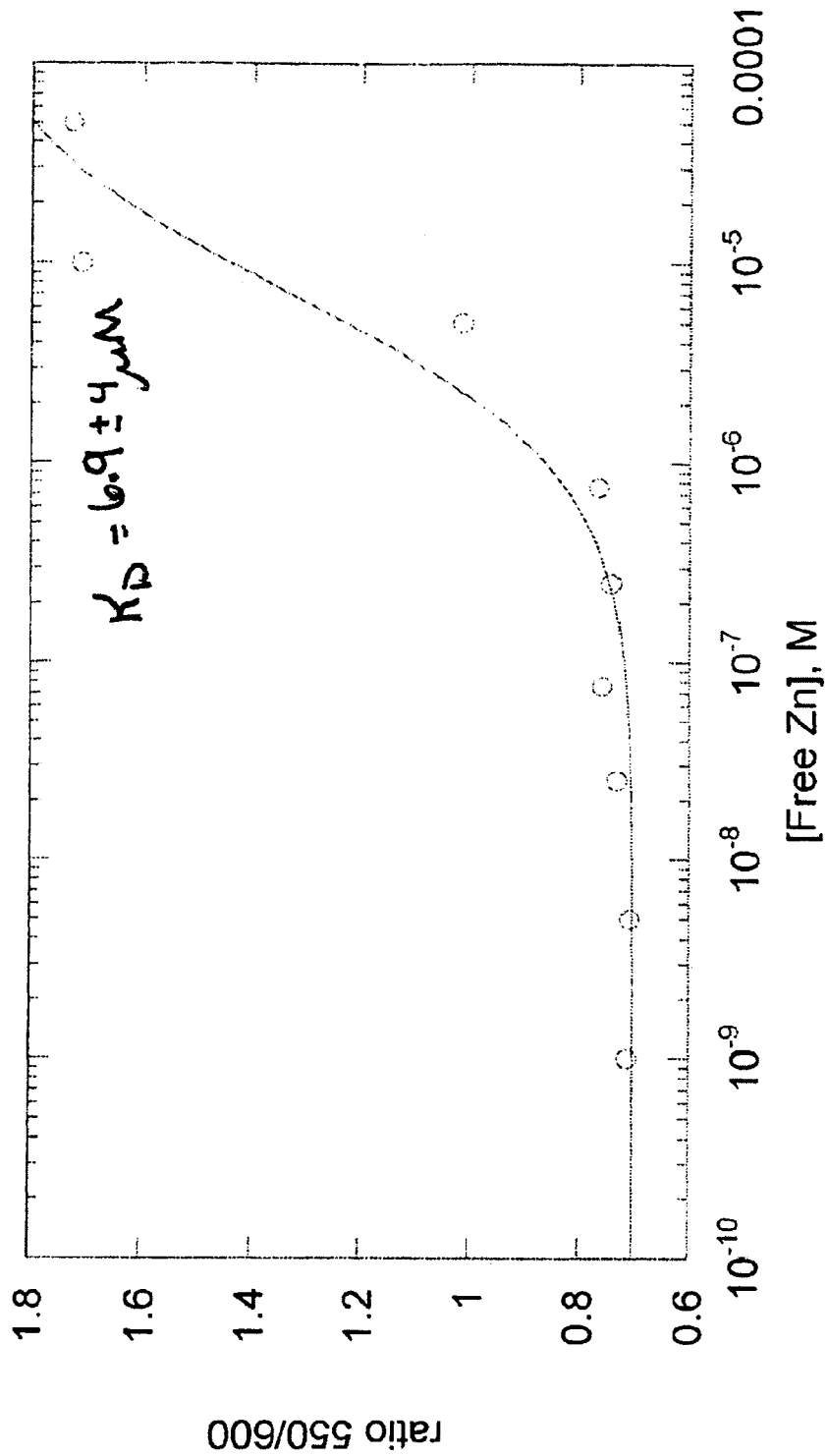
FIG. 13 depicts a fluorescence intensity ratio of ABD-N labeled H94N apocarbonic anhydrase II (CA) as a function of free zinc [Zn(11)] concentration.

In this example, 5 μM apoH94N human CA II was coentrapped in a sensor device in a 7% polyacrylamide gel that is 10 mM of a citrate buffer at pH 7.5 and 100 mM NaCl with 10 μM poly-ABD-N, and put in contact with an aqueous sample having a free zinc concentration of approximately 5 nanomolar. The device was excited with an excitation source (such as a 408 nm diode laser) and the fluorescence intensities were measured though interference filters whose peak transmissions are approximately 550 nm and 600 nm, and their ratio determined. The free zinc ion concentration to which the device was exposed was measured by comparison with the same measurement performed on devices contacted with zinc solutions having known free zinc ion concentrations formulated by methods well known in the art (R. B. Thompson, et al., Journal of Neuroscience Methods Vol. 96, pages 35-45 (2000), incorporated herein by reference). FIG. 13 depicts a fluorescence intensity ratio of poly-ABD-N and H94N apocarbonic anhydrase II (CA) as a function of free zinc [Zn(11)] concentration.

Table 1 below sets forth the raw data depicted in the graph of FIG. 13. From the data, the inventors determined a binding isotherm and extracted an apparent $K_D$ of $6.9 \times 10^{-6} \pm 4$ μM.

TABLE 1

| H94N in citrate buffers | | | |
|---|---|---|---|
| [Free Zn], M | 550 | 600 | Ratio 550/600 |
| 1.0000e−09 | 45.000 | 63.000 | 0.71429 |
| 4.9900e−09 | 39.000 | 55.000 | 0.70909 |
| 2.5100e−08 | 33.000 | 45.000 | 0.73333 |
| 7.5100e−08 | 38.000 | 50.000 | 0.76000 |
| 2.5000e−07 | 35.000 | 47.000 | 0.74468 |
| 7.5100e−07 | 33.000 | 43.000 | 0.76744 |
| 5.0100e−06 | 67.000 | 66.000 | 1.0152 |
| 1.0000e−05 | 250.00 | 146.00 | 1.7123 |
| 5.0000e−05 | 190.00 | 110.00 | 1.7273 |

Figure 14:
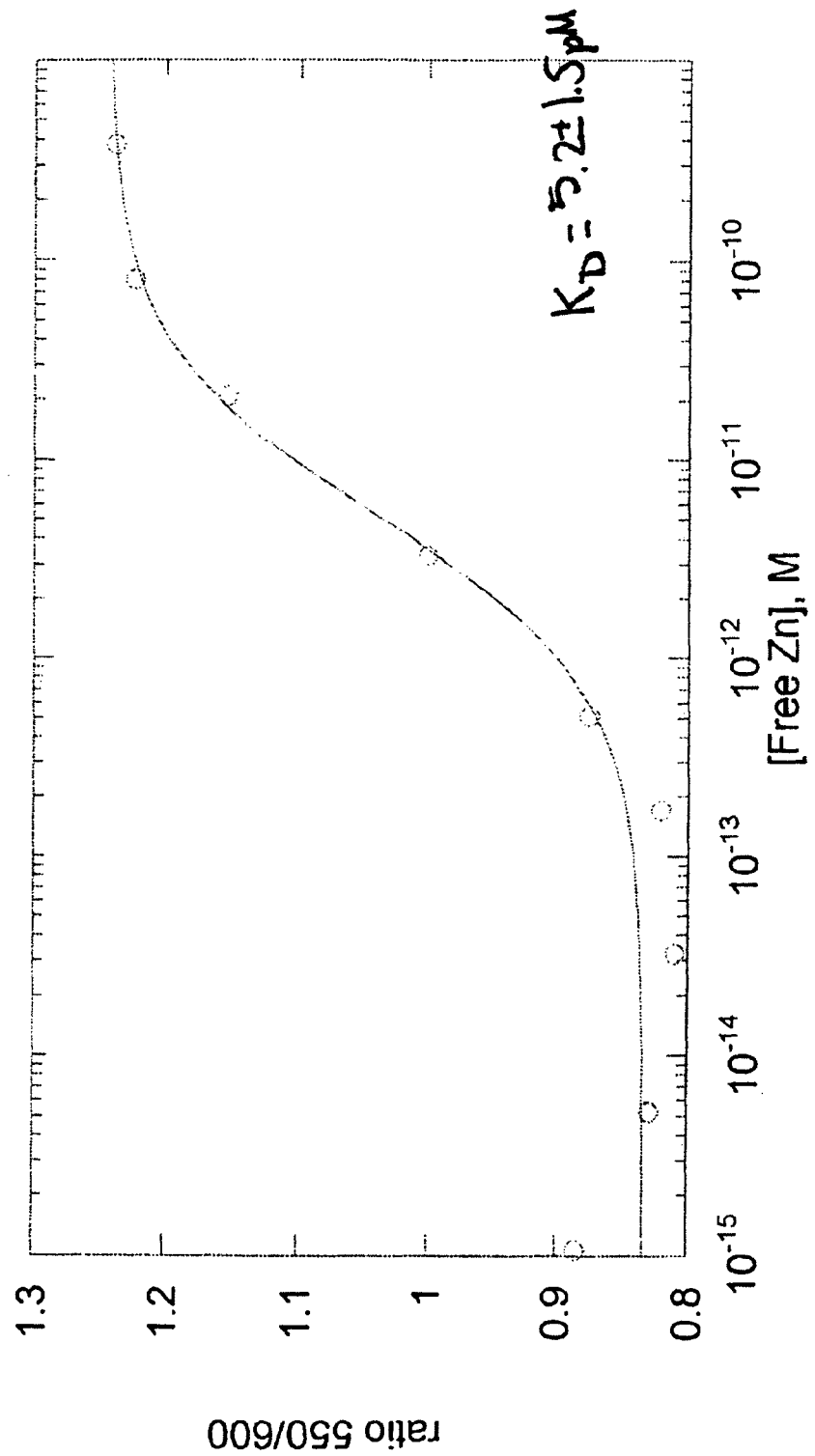
FIG. 14 depicts a fluorescence intensity ratio of ABD-N labeled wild type apocarbonic anhydrase II (CA) as a function of free zinc [Zn(11)] concentration.

Similarly, Wild Type human CA II was entrapped in a sensor device in a polyacrylamide gel. In this experiment the metal ion buffer is an NTA/DPA buffer. The device was then put in contact with an aqueous sample having a free zinc concentration of approximately 5 picomolar. The device was excited with an excitation source (such as a 408 nm diode laser) and the fluorescence intensities measured though interference filters whose peak transmissions are approximately 550 nm and 600 nm, and their ratio determined. The free zinc ion concentration to which the device was exposed was measured by comparison with the same measurement performed on devices contacted with zinc solutions having known free zinc ion concentrations formulated by methods well known in the art. FIG. 13 depicts a fluorescence intensity of ABD-N labeled H94N apocarbonic anhydrase II (CA) as a function of free zinc [Zn(11)] concentration. FIG. 14 depicts a fluorescence intensity ratio of ABD-N labeled wild type apocarbonic anhydrase II (CA) as a function of free zinc [Zn(11)] concentration.

Table 2 below sets forth the raw data depicted in the graph of FIG. 14. From the data, the inventors determined a binding isotherm and extracted an apparent $K_D$ of $5.2 \times 10^{-12} \pm 1.5$ pM.

TABLE 2

| Wild Type CA in NTA/DPA buffers | | | |
|---|---|---|---|
| [Free Zn], M | 550 | 600 | Ratio 550/600 |
| 1.0600e−15 | 46.000 | 52.000 | 0.88462 |
| 5.2300e−15 | 34.000 | 41.000 | 0.82927 |
| 3.2100e−14 | 34.000 | 42.000 | 0.80952 |
| 1.7000e−13 | 41.000 | 50.000 | 0.82000 |
| 5.1000e−13 | 35.000 | 40.000 | 0.87500 |
| 3.2900e−12 | 61.000 | 61.000 | 1.0000 |
| 2.0900e−11 | 75.000 | 65.000 | 1.1538 |
| 7.9700e−11 | 82.000 | 67.00 | 1.2239 |
| 3.7800e−10 | 88.000 | 71.00 | 1.2394 |

The two experiments in this Example show that by changing the binding entity/binding protein, one can vary to which approximate concentration of free zinc, a sensor device of the present invention may be sensitive. Accordingly, if one knows an approximate concentration of a particular analyte in a sample, one may select an appropriate binding entity to make the sensor device sensitive to that concentration.

EXAMPLE 4

In this example, human apocarbonic anhydrase II variant L198C fluorescent labeled with Alexa Fluor 660 maleimide is entrapped at 1 μM within a sensor device in a polyacrylamide gel comprising 7% acrylamide monomer and 0.2% N,N-methylene bis acrylamide in pH 7.5 seawater buffer. After contacting the sensor device with an aqueous sample such as sea water having a known free copper concentration, the proportion of the protein with target analyte, Cu(II), bound in the active site is quantitated by measuring the proportion with a short (0.3 nsec) vs. unquenched (1.7 nsec) lifetime by mounting the sensor in a phase fluorometer configured as in FIG. 4, with a 655 nm diode laser excitation source and measuring the frequency-dependent phase and modulation through a 682DF22 emission filter. The proportion of protein with Cu(II) bound (and thus the free Cu(II) concentration to which the device was exposed) was measured by measuring the phases and comparing them to those measured for the device in copper-buffered calibration standards, which are formulated using methods known in the art, as previously described (H. H. Zeng, et al., Analytical Chemistry, Vol. 75, pp. 6807-12 (2003), incorporated herein by reference).

Figure 15:
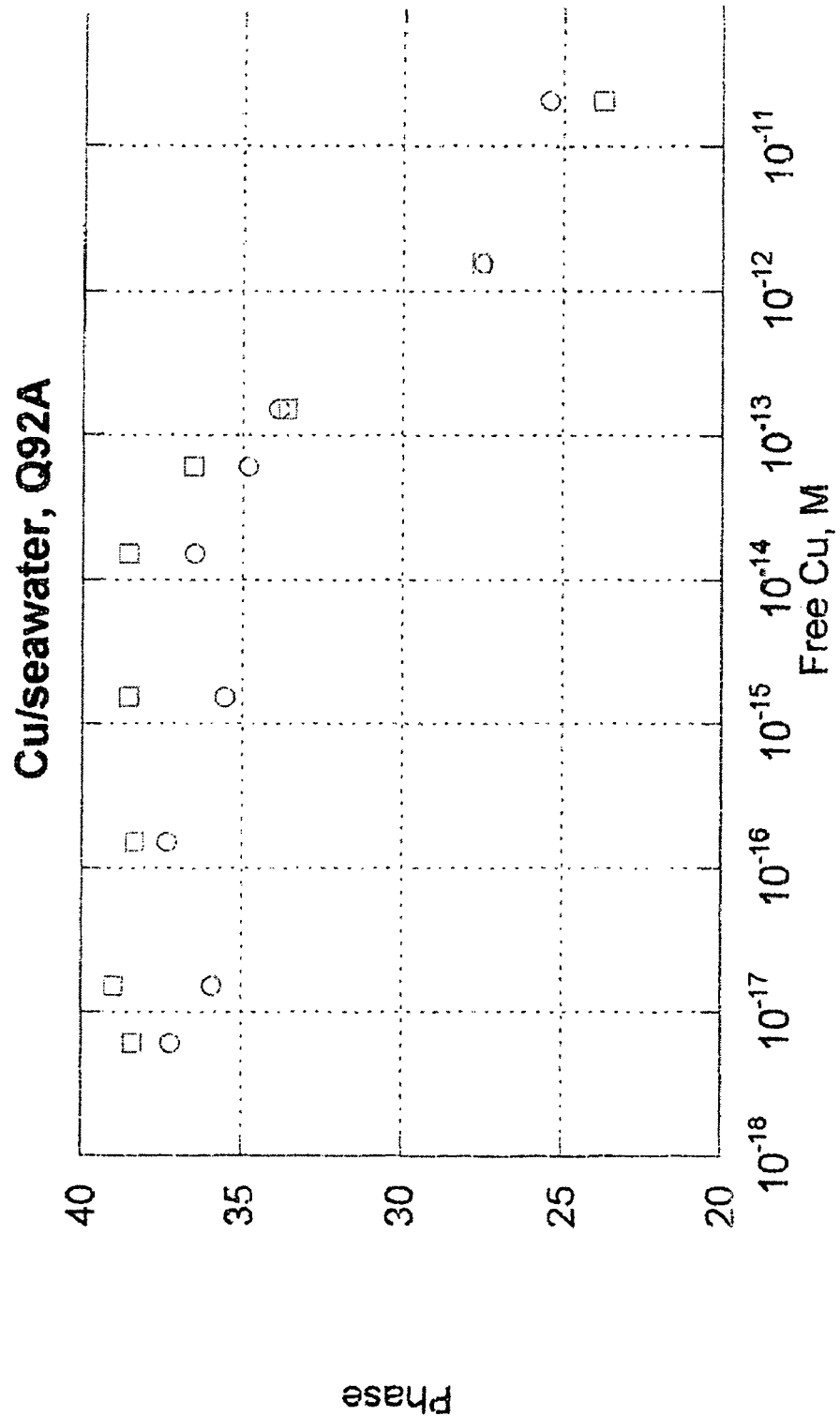
FIG. 15 plots the phase angle of human apocarbonic anhydrase II variant L198C labeled with Alexa Fluor 660 as a function of free copper ion concentration, as measured by each of a commercial fluorometer (C) and using the devices of the present invention (B).

FIG. 15 plots the phase angle (in degrees) of human apocarbonic anhydrase II variant L198C labeled with Alexa Fluor 660 as a function of free copper ion concentration, as measured by each of a commercial fluorometer (C) and using the devices of the present invention (B). The modulation frequency was 84 MHz.

This experiment confirms that the response of sensor devices of the present invention reveal comparable results to the response of a commercial fluorometer device. The experiment also shows that the present sensor devices can measure in very low analyte concentrations.

Sensor devices of the present invention can be deployed in the environment and can equilibrate with a free copper concentration. Sensor devices of the present invention can also be used in a small sample size.

Although the invention has been described in example embodiments, many additional modifications and variations would be apparent to those skilled in the art. For example, modifications may be made to the methods described herein including the addition of or changing the order of various steps. Also, components may be added to the optical systems. It is therefore to be understood that this invention may be practiced other than as specifically described. Thus, the present embodiments should be considered in all respects as illustrative and not restrictive.

What is claimed is:

1. A sensor device comprising
   an essentially disk-shaped substrate having at least one hole extending through the substrate approximately at a center of the substrate; and having at least one binding entity immobilized in a matrix entrapped in the hole, wherein the binding entity comprises a macromolecule and at least one photoluminescent label,
   wherein the binding entity comprises at least one binding site that selectively binds at least one target analyte, and is capable of generating a detectable signal upon binding of a target analyte to said binding entity, wherein the target analyte comprises a metal ion; and
   wherein the sensor device is adapted in shape, size, and placement of the binding entity thereon such that the sensor device is capable of being mounted in an optical system to position the binding entity substantially at a focus of an objective in the optical system to detect the detectable signal.

2. The sensor device of claim 1, wherein the sensor device comprises at least one material selected from the group consisting of PTFE, glass, fused silica, polycarbonate, and plasma-treated polystyrene.

3. The sensor device of claim 1, wherein the macromolecule comprises one or more molecules selected from the group consisting of apocarbonic anhydrase, phosphatase, leucine aminopeptidase, carboxypeptidases, laccases, azurins, ureases, and mutants and variants thereof.

4. The sensor device of claim 1, wherein each binding entity is present in an amount of less than one picomole.

5. The sensor device of claim 1, wherein the matrix comprises a gel.

6. The sensor device of claim 1, comprising at least two binding entities, wherein each binding entity is capable of binding to a different target analyte.

7. The sensor device of claim 1, wherein the metal ion comprises at least one metal ion selected from the group consisting of Zn(II), Cu(II), Cd(II), Co(II), Ni(II), Fe(II), Mn(II), Pb(II), and Hg(II).

8. The sensor device of claim 1, wherein the at least one hole comprises a conical opening.

* * * * *